US 10,174,056 B2

United States Patent
Wu et al.

(10) Patent No.: US 10,174,056 B2
(45) Date of Patent: Jan. 8, 2019

(54) SUBSTITUTED PYRROLO[2,3-D]PYRIMIDINES AS JANUS KINASE INHIBITORS

(71) Applicant: WUXI FORTUNE PHARMACEUTICAL CO., LTD, Jiangsu (CN)

(72) Inventors: Hao Wu, Shanghai (CN); Weiwei Mao, Shanghai (CN); Yiqiang Huang, Shanghai (CN); Lili Fan, Shanghai (CN); Shuhui Chen, Shanghai (CN)

(73) Assignee: WUXI FORTUNE PHARMACEUTICAL CO., LTD, Jiangsu (CN)

( * ) Notice: Subject to any disclaimer, the term of this patent is extended or adjusted under 35 U.S.C. 154(b) by 0 days.

(21) Appl. No.: 15/577,674

(22) PCT Filed: May 26, 2016

(86) PCT No.: PCT/CN2016/083426
§ 371 (c)(1),
(2) Date: Nov. 28, 2017

(87) PCT Pub. No.: WO2016/192563
PCT Pub. Date: Dec. 8, 2016

(65) Prior Publication Data
US 2018/0162879 A1     Jun. 14, 2018

(30) Foreign Application Priority Data

May 29, 2015    (CN) .......................... 2015 1 0289933
May 23, 2016    (CN) .......................... 2016 1 0344370

(51) Int. Cl.
| | |
|---|---|
| *A61K 31/519* | (2006.01) |
| *C07D 487/04* | (2006.01) |
| *C07D 519/00* | (2006.01) |
| *A61P 19/02* | (2006.01) |

(52) U.S. Cl.
CPC .......... *C07D 519/00* (2013.01); *A61K 31/519* (2013.01); *A61P 19/02* (2018.01); *C07D 487/04* (2013.01)

(58) Field of Classification Search
CPC .......................... A61K 31/519; C07D 487/04
USPC ....................................... 514/265.1; 544/280
See application file for complete search history.

(56) References Cited

U.S. PATENT DOCUMENTS

| | | | |
|---|---|---|---|
| 7,301,023 B2 | 11/2007 | Flanagan et al. | |
| 8,808,764 B2 | 8/2014 | Heaton et al. | |
| 2002/0094974 A1 | 7/2002 | Castelhano et al. | |
| 2013/0131039 A1 | 5/2013 | Burgess et al. | |
| 2014/0228349 A1 | 8/2014 | Boys et al. | |

FOREIGN PATENT DOCUMENTS

| | | |
|---|---|---|
| CN | 1489590 A | 4/2004 |
| CN | 1729192 A | 2/2006 |
| CN | 102985424 A | 3/2013 |
| CN | 103987713 A | 8/2014 |
| WO | 2002096909 A1 | 12/2002 |
| WO | 2009047514 A1 | 4/2009 |
| WO | 2010020905 A1 | 2/2010 |
| WO | 2015087201 A1 | 6/2015 |

OTHER PUBLICATIONS

Baxter EJ, et al., "Acquired mutation of the tyrosine kinase JAK2 in human myeloproliferative disorders", Lancet. 2005; 365 (9464): 1054-61.
Berge et al., "Pharmaceutical Salts", Journal of Pharmaceutical Science 66: 1-19 (1977).
European Search Report dated Jun. 28, 2018 from European Application No. 16739772.8.
Flanagan et al., "Discovery of CP-690,550: A Potent and Selective Janus Kinase (JAK) Inhibitor for the Treatment of Autoimmune diseases and Organ Transplant Rejection", Journal of Medicinal Chemistry, vol. 53, No. 24, Dec. 23, 2010, pp. 8468-8484.
Hubert Maehr, "A Proposed New Convention for Graphic Presentation of Molecular Geometry and Topography", J. Chem. Ed. 1985, 62: 114-120.
International Search Report & Written Opinion dated Jun. 30, 2016 from PCT Application No. PCT/CN2016/080208.
International Search Report & Written Opinion dated Sep. 1, 2016 from PCT Application No. PCT/CN2016/083426.
International Search Report & Written Opinion from corresponding International PCT Application No. PCT/CN2016/071313.
Levy et al., "STAT3 Signaling and the Hyper-IgE Syndrome", N Engl J Med 2007; 357:1655-1658Oct. 18, 2007DOI: 10.1056/NEJMe078197.
Linda M. Scott et al., "JAK2 Exon 12 Mutations in Polycythemia Vera and Idiopathic Erythrocytosis", NEngl J Med 2007;356:459-68.

(Continued)

*Primary Examiner* — Douglas M Willis
(74) *Attorney, Agent, or Firm* — Innovation Capital Law Group, LLP; Vic Lin

(57) ABSTRACT

A compound having the structure of below Formula(I), or pharmaceutically acceptable salts thereof, are useful as Janus kinase inhibitors, wherein $R_1$ and $L_1$ are as herein described.

20 Claims, No Drawings

(56) References Cited

OTHER PUBLICATIONS

O Kilpivaara et al., "JAK2 and MPL mutations in myeloproliferative neoplasms: discovery and science", Leukemia (2008) 22, 1813-1817.

O'Shea, "Targeting the Jak/STAT pathway for immonusuppression", Ann Rheum Dis 2004;63(Suppl II):ii67-ii71. doi: 10.1136/ard2004.028290.

Remington, "The Science and Practice of Pharmacy", 21st Ed., Lippincott, Williams & Wilkins (2005).

Vainchenker W, et al., "Constantinescu SNJAKs in pathology: role of Janus kinases in hematopoietic malignancies and immunodeficiencies", Semin Cell Dev Biol 19:385-393 (http://www.sciencedirect.com/science/journal/10849521/19/4?sdc=1).

SUBSTITUTED PYRROLO[2,3-D]PYRIMIDINES AS JANUS KINASE INHIBITORS

FIELD OF THE INVENTION

The present invention relates to a series of Janus kinase inhibitors, in particular to compounds of Formula (I) or pharmaceutically acceptable salts thereof.

BACKGROUND OF THE INVENTION

JAK belongs to a family of tyrosine kinases that are involved in inflammation, autoimmune diseases, proliferative diseases, transplant rejection, diseases involving impairment of cartilage turnover, congenital cartilage malformations and/or diseases associated with hypersecretion of IL6. The present invention also provides methods for the production of the compounds, pharmaceutical compositions comprising the compounds, methods for the prophylaxis and/or treatment of diseases involving inflammation, autoimmune diseases, proliferative diseases, transplant rejection, diseases involving impairment of cartilage turnover, congenital cartilage malformations and/or diseases associated with hypersecretion of IL6 by administering a compound of the present invention.

Janus kinases (JAK) are cytoplasmic tyrosine kinases that transduce cytokine signaling from membrane receptors to STAT transcription factors. Four JAK family members are described in the prior art: JAK1, JAK2, JAK3 and TYK2. Upon binding of the cytokine to its receptor, JAK family members auto- and/or transphosphorylate each other, followed by phosphorylation of STATs and then migrate to the nucleus to modulate transcription. JAK-STAT intracellular signal transduction is suitable for the interferons, most interleukins, as well as a variety of cytokines and endocrine factors such as EPO, TPO, GH, OSM, LIF, CNTF, GM-CSF and PRL (Vainchenker W. et al. (2008)).

The combination of genetic models and small molecule JAK inhibitor research revealed the therapeutic potential of several JAKs. JAK3 is validated by mouse and human genetics as an immune-suppression target (O'Shea J et al. (2004)). JAK3 inhibitors were successful taken into clinical development, initially for organ transplant rejection but later also in other immuno-inflammatory indications such as rheumatoid arthritis (RA), psoriasis and Crohn's diseases (http://clinicaltrials.gov/). TYK2 is a potential target for immuno-inflammatory diseases, being validated by human genetics and mouse knock-out studies (Levy D. and Loomis C. (2007)). JAK1 is a new target in the immuno-inflammatory disease area. JAK1 heterodimerizes with other JAKs to transduce cytokine-driven pro-inflammatory signaling. Therefore, it is expected that inhibition of JAK1 and other JAKs are a therapeutic benefit for a series of inflammatory diseases and other diseases driven by JAK-mediated signal transduction.

BRIEF SUMMARY OF THE INVENTION

It is an object of this invention to provide a compound of Formula (I) or a pharmaceutically acceptable salt thereof,

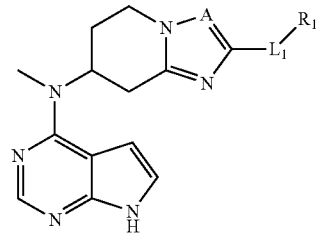

wherein,

R is selected from C(R) or N;

$L_1$ is selected from a single bond, —C(=O)O—, —C(=O)—, —S(=O)—, —S(=O)$_2$—, —C(=O)N(R)—, —N(R)C(=O)N(R)—, —N(R)—, —S(=O)N(R)—, —S(=O)$_2$N(R)C(R)$_2$—, —S(=O) N(R)C(R)$_2$—;

$R_1$ is selected from H, CN, OH, NH$_2$, halogen, or is selected from: $C_{1-6}$ alkyl, $C_{1-6}$ heteroalkyl, $C_{3-6}$ cycloalkyl, 3-6 membered heterocycloalkyl, which can be optionally substituted with 1, 2, 3, or 4 R;

R is independently selected from H, CN, OH, NH$_2$, halogen, or is independently selected from: $C_{1-6}$ alkyl, $C_{1-6}$ heteroalkyl, which can be optionally substituted with 1, 2, 3, or 4 R';

R' is selected from halogen, OH, NH$_2$, CN, Me, Et, CF$_3$, CH$_2$CF$_3$, NHCH$_3$, N(CH$_3$)$_2$; the "hetero" is selected from heteroatoms or heterogroups, and is selected from N, O, S, —C(=O)O—, —C(=O)—, —S(=O)—, —S(=O)$_2$—, the number of "hetero" in any of the above conditions is independently selected from 1, 2, or 3.

In some embodiments of the invention, R is selected from H, CN, OH, NH$_2$, halogen, or is selected from: Me, Et, NHCH$_3$, N(CH$_3$)$_2$, NHCH$_3$, NH(CH$_3$)$_2$,

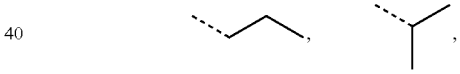

which can be optionally substituted with 1, 2, or 3 R'.

In some embodiments of the invention, $L_1$ is selected from a single bond, —C(=O)O—, —C(=O)—, —S(=O)—, —S(=O)$_2$—, —C(=O)NH—, —NHC(=O)NH—, —NH—, —S(=O)NH—, S(=O)$_2$NHCH$_2$—, —S(=O)NHCH$_2$—.

In some embodiments of the invention, $R_1$ is selected from CN, OH, NH$_2$, or is selected from: $C_{1-3}$ alkyl, $C_{1-2}$ alkyl-N($C_{1-2}$ alkyl)$_2$, $C_{1-2}$ alkyl-NH—$C_{1-2}$ alkyl, $C_{1-3}$ alkyl-S(=O)$_2$C$_{1-3}$ alkyl, $C_{1-3}$ alkyl-S(=O)—$C_{1-3}$ alkyl, $C_{4-5}$ cycloalkyl, 4-5 membered heterocycloalkyl, which can be optionally substituted with 1, 2, 3, or 4 R.

In some embodiments of the invention, $R_1$ is selected from CN, or is selected from: Me, Et,

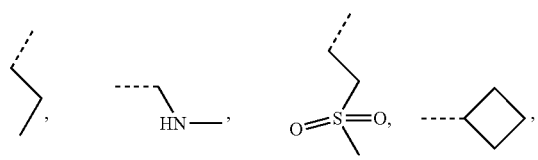

which can be optionally substituted with 1, 2, 3, or 4 R.

In some embodiments of the invention, $R_1$ is selected from CN, Me,
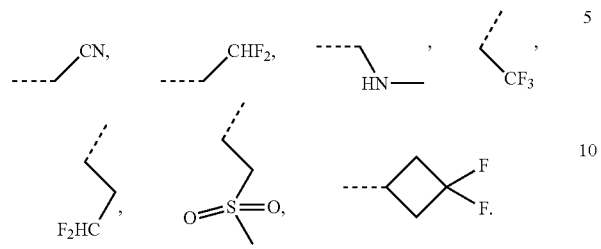
The compound of the invention is selected from:
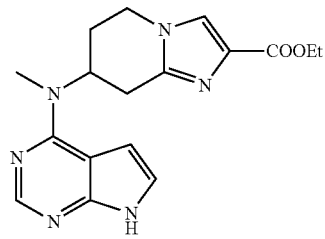
WX550
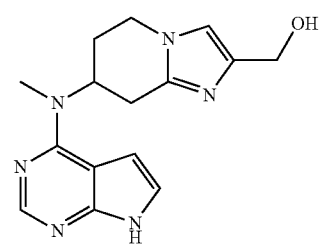
WX551
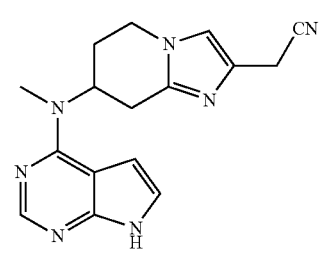
WX552
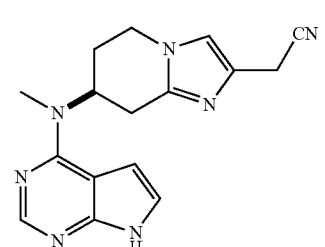
WX612
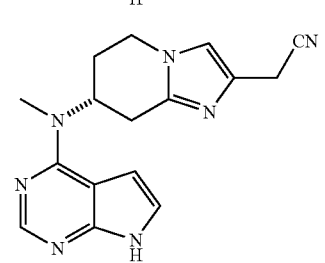
WX613
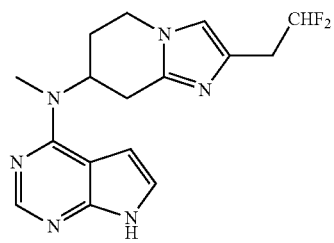
WX611
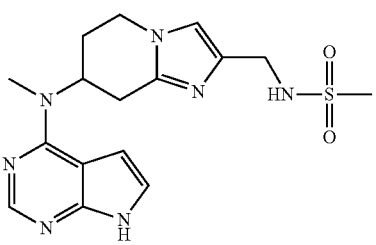
WX606
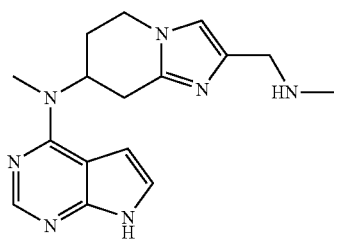
WX605
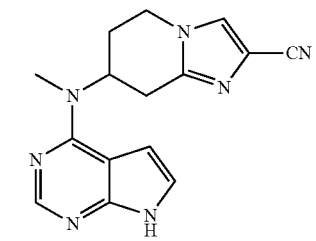
WX591
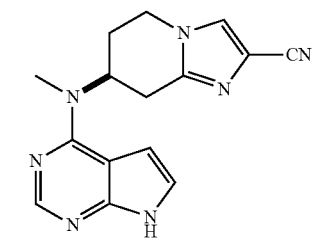
WX614
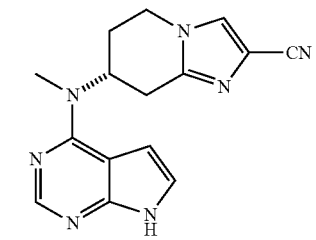
WX615

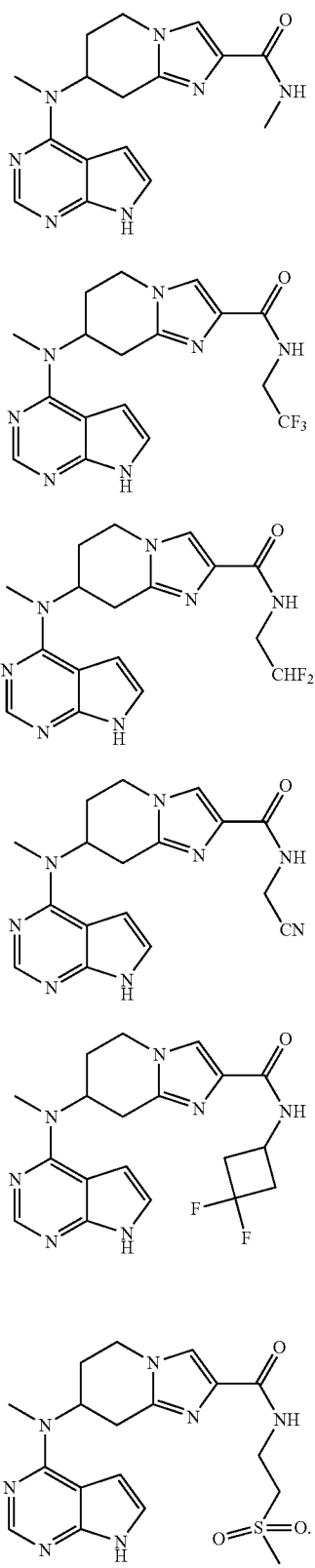

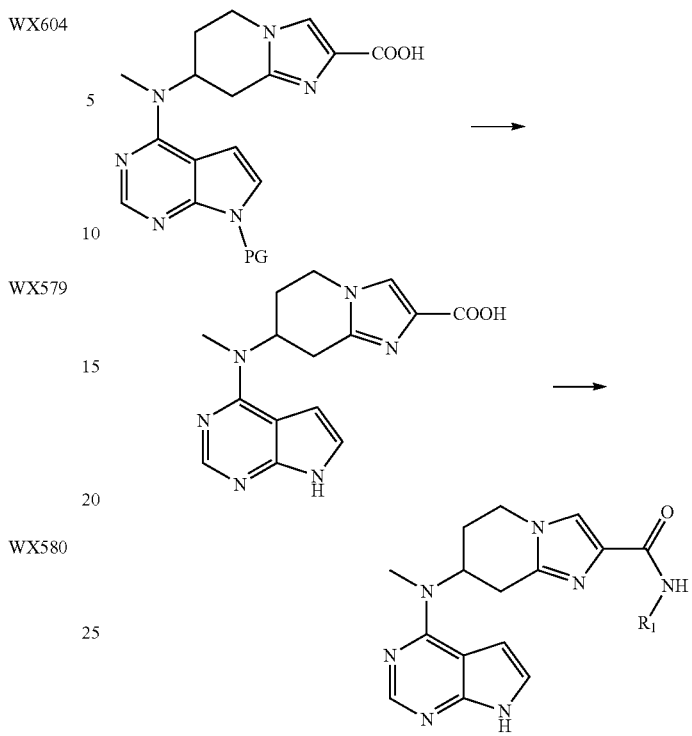

wherein, PG is an amino-protecting group, and is selected from benzyloxycarbonyl (Cbz), tert-butoxycarbonyl (Boc), fluorenylmethoxycarbonyl (Fmoc), allyloxycarbonyl (Alloc), trimethylethoxycarbonyl (Teco), methoxycarbonyl, ethoxycarbonyl, o-phthalyl (Pht), p-toluenesulfonyl (Tos), trifluoroacetyl (Tfa), benzyl (Bn), p-methoxybenzyl (PMB).

The present invention also provides a pharmaceutical composition, comprising: a therapeutically effective amount of the above compound or a pharmaceutically acceptable salt thereof, and a pharmaceutically acceptable carrier.

The present invention also provides that, use of the above compound or a pharmaceutically acceptable salt thereof, or the above pharmaceutical composition for manufacturing a medicament for treating Janus kinase-related diseases.

In some embodiments of the invention, the above disease is arthritis.

In some embodiments of the invention, the above disease is rheumatoid arthritis.

Definitions

Unless specified otherwise, the following terms and phrases used herein are intended to have the following meanings. A specific term or phrase should not be considered to be uncertain or unclear without specific definition, but should be understood in its general meanings. When a trade name appears herein, it is intended to refer to its corresponding commodity or its active ingredient. As used herein, the term "pharmaceutically acceptable" is employed to refer to those compounds, materials, compositions and/or dosage forms which are, within the scope of reliable medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" refers to salts of the compound of the present invention, which are The present invention also provides a method of making the compound of Formula (I), comprising the following steps:

prepared from the compounds having particular substituent found by the present invention with relatively nontoxic acids or bases. When compounds of the present invention contain relatively acidic functionalities, base addition salts can be obtained by contacting a sufficient amount of the base with the neutral form of such compounds, either in a neat solution or in a suitable inert solvent. The pharmaceutically acceptable base addition salts include sodium, lithium, calcium, ammonium, organic ammonium, magnesium, and the like. When compounds of the present invention contain relatively basic functionalities, acid addition salts can be obtained by contacting a sufficient amount of the acid with the neutral form of such compounds, either in a neat solution or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic acids and the like (see, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

Preferably, the neutral forms of the compounds may be regenerated by contacting the salt with a base or acid and isolating the parent compound in the conventional manner. The parent form of the compound differs from the various salt forms in certain physical properties, such as solubility in polar solvents.

As used herein, "pharmaceutically acceptable salts" belongs to derivatives of the disclosed compounds wherein the parent compound is modified by converting an existing acid or base to its salt form. Examples of pharmaceutically acceptable salts include, but not limited to, inorganic or organic acid salts of basic residues such as amines; alkali or organic salts of acidic residues such as carboxylic acids, and the like. The pharmaceutically acceptable salts include the conventional non-toxic salts or the quaternary ammonium salts of the parent compounds formed, for example, from non-toxic inorganic or organic acids. Such conventional non-toxic salts include, but not limited to, those derived from salts of inorganic or organic acids selected from 2-acetoxybenzoic, 2-hydroxyethane sulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, hydrobromic, hydrochloric, hydroiodic, hydroxy, hydroxynaphthoic, isethionic, lactic, lactobionic, lauryl sulfonic, maleic, malic, mandelic, methane sulfonic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and p-toluenesulfonic acids.

The pharmaceutically acceptable salts of the present invention can be synthesized from the parent compound which contains an acidic or basic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, iso-propanol, or acetonitrile are preferred.

In addition to salt forms, the compounds provided by the present invention are also in the form of prodrugs. The prodrugs of the compounds described herein are those compounds that readily undergo chemical changes under physiological conditions to convert to the compounds of the present invention. Additionally, prodrugs can be converted to the compounds of the present invention by chemical or biochemical methods in vivo environment.

The compounds of the present invention can exist in unsolvated forms as well as solvated forms, which including hydrated forms. In general, the solvated forms are equivalent to unsolvated forms and are intended to be encompassed within the scope of the present invention.

Certain compounds of the present invention possess asymmetric carbon atoms (optical centers) or double bonds. The racemates, diastereomers, geometric isomers and individual isomers are all intended to be encompassed within the scope of the present invention.

The graphic representations of racemic, ambiscalemic and scalemic or enantiomerically pure compounds used herein are taken from: Maehr, J. Chem. Ed. 1985, 62: 114-120. Unless specified otherwise, wedges and broken lines are used to denote the absolute configuration of a stereocenter. When the compounds described herein contain olefinic double bonds or other centers of geometric asymmetry, and unless specified otherwise, it is intended to include both E and Z geometric isomers. All tautomers are encompassed by the present invention as well.

The compounds of the present invention may exist in particular geometric or stereoisomeric forms. The present invention takes into account all such compounds, including cis- and trans isomers, (−)- and (+)-pair enantiomers, (R)- and (S)-enantiomers, diastereomers, (D)-isomers, (L)-isomers, the racemic mixture thereof and other mixture, such as the enriched mixture of either the enantiomers or the diastereomers, as being covered within the scope of this invention. Additional asymmetric carbon atoms may be present in a substituent such as an alkyl group. All such isomers, as well as mixtures thereof, are intended to be included in this invention.

Optically-active (R)- and (S)-enantiomers, and D-, and L-isomers may be prepared by chiral synthesis, or by chiral reagents, or by any other conventional techniques. If an enantiomer of a certain compound of the present invention is desired, it may be prepared by asymmetric synthesis, or by derivation with a chiral auxiliary, where the resulting diastereomeric mixture is separated and the auxiliary group cleaved to provide the pure desired enantionmers. Alternatively, where the molecule contains a basic functional group, such as amino, or an acidic functional group, such as carboxyl, diastereomeric salts are formed with an appropriate optically-active acid or base, followed by resolution of the diastereomers thus formed by resolution means well known in the art, and subsequent recovery of the pure enantionmers. Additionally, the separation of the enantionmers and diastereomers can be generally accomplished by using chromatography which using chiral stationary phase and optionally in combination with a chemical derivatization method (e.g. the formation of carbamates from amines).

The compounds of the present invention may also contain unnatural proportions of atomic isotopes at one or more of the atoms that constitute such compounds. For example, the compounds may be labeled by using radioactive isotopes, such as tritium ($^3H$), iodine-125 ($^{125}I$), or carbon-14 ($^{14}C$). All isotopic variations of the compounds of the present invention, whether radioactive or not, are intended to be encompassed within the scope of the present invention.

The term "pharmaceutically acceptable carriers" refers to any formulation or carrier medium capable of delivering an effective amount of the active substance of the present invention without interfering with the biological activity of the active substance and having no toxic side effects to the host or patient. The representative carriers include water, oils, vegetables and minerals, cream base, lotion matrix, ointment matrix, and the like. These matrices include suspending agents, tackifiers, transdermal enhancers, and the like, the formulations of which are well known to those skilled person in the art of cosmetics or local medicines. Regarding additional information about the carriers, refer to the content in "Remington: The Science and Practice of Pharmacy, 21 st Ed., Lippincott, Williams & Wilkins (2005)" which are hereby incorporated by reference.

The term "excipient" generally refers to the carrier, diluent and/or medium required by preparation of an effective pharmaceutical composition.

For the drug or pharmacologically active agent, the term "effective amount" or "therapeutically effective amount" refers to a nontoxic but sufficient amount of the drug or agent to provide the desired effect. For the oral dosage in the present invention, the "effective amount" of an active substance in the composition refers to the amount required to achieve the desired effect when used in combination with another active substance in the composition. The effective amount will vary from subject to subject, depending on the age and general condition of the individual, depending on the particular active agent as well. An appropriate "effective" amount in any individual case may be determined by one of ordinary skill in the art in accordance with conventional experimentation.

The terms "active ingredient", "therapeutic agent", "active substance" or "active agent" mean a chemical entity which is effective in treating a target disorder, disease or condition.

The term "substituted" means that any one or more hydrogen atoms on the designated atom is replaced with substituent, provided that the designated atom's valency is normal, and that the substitution results in a stable compound. When the substituent is keto (i.e., =O), then two hydrogen atoms are substituted. Keto substituents are not present on aromatic moieties. The term "optionally substituted" means that it may be substituted or may not be substituted, unless specified otherwise, the type and number of substituents may be optionally on the chemically achievable basis.

When any variable (e.g., R) occurs more than one time in constituent or formula for a compound, its definition at each occurrence is independent. Thus, for example, if a group is shown to be substituted with 0-2 R, then said group may optionally be substituted with up to two R groups and R at each occurrence is selected independently from the definition of R. Also, combinations of substituents and/or variables are permissible only if such combinations result in stable compounds.

When the number of a linking group is 0, such as —(CRR)$_0$—, it indicates that the linking group is a single bond.

When one of the variables is selected from a single bond, it indicates that the two groups to which they are attached are directly connected, for example, when L in A-L-Z represents a single bond, the structure is actually A-Z.

When a substituent is vacant, it indicates that the substituent is absent, for example, when X is vacant in A-X, it means that the structure is actually A. When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds. For example, the structural unit

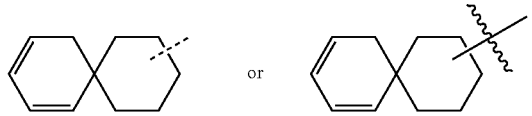

indicates that it can be substituted at any position on the cyclohexyl group or the cyclohexadiene group.

Unless specified otherwise, the term "hetero" means a heteroatom or heteroatom radical (i.e., an atomic radical containing a heteroatom), including atoms other than carbon (C) and hydrogen (H), and atomic radical containing such heteroatoms, for example, including oxygen (O), nitrogen (N), sulfur (S), silicon (Si), germanium (Ge), aluminum (Al), boron (B), —O—, —S—, =O, =S, —C(=O)O—, —C(C=O)—, —S(=O), —S(=O)$_2$—, and optionally substituted —C(=O)N(H)—, —N(H)—, —C(=NH)—, —S(=O)$_2$N(H)— or —S(=O)N(H)—.

Unless specified otherwise, "cyclo" refers to a substituted or unsubstituted cycloalkyl, heterocycloalkyl, cycloalkenyl, heterocycloalkenyl, cycloalkynyl, heterocycloalkynyl, aryl or heteroaryl. The ring includes monocyclic ring, bicyclic ring, spiro ring, or bridged ring. The number of atoms on the ring is usually defined as the number of membered ring, for example, "5- to 7-membered ring" refers to the surrounding arrangement of 5 to 7 atoms. Unless specified otherwise, the ring optionally contains from 1 to 3 heteroatoms.

Thus, the term "5- to 7-membered ring" includes such as phenyl, pyridyl and piperidinyl. On the other hand, the term "5- to 7-membered heterocycloalkyl ring" includes pyridyl and piperidinyl, but does not include phenyl. The term "cyclo" also includes cyclic system containing at least one ring, in which each "cyclo" independently meets the above definition.

Unless specified otherwise, the term "heterocycle" or "heterocyclic group" is intended to mean a stable monocyclic or bicyclic or tricyclic ring, including heteroatom or heteroatom radical, which is saturated, partially unsaturated or fully unsaturated (aromatic), and which consists of carbon atoms and from 1, 2, 3 or 4 cyclic heteroatoms independently selected from the group consisting of N, O and S; and including any bicyclic group in which any of the above-defined heterocyclic rings is fused to a benzene ring. The nitrogen and sulfur heteroatoms may optionally be oxidized (NO, and S(O)p, p represents 1 or 2). The nitrogen atom may be substituted or unsubstituted (i.e., N or NR, wherein R is H or other substituents already defined herein). The heterocyclic ring may be attached to its pendant group at any heteroatom or carbon atom which results in a stable structure. The heterocyclic ring described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl group" is intended to mean a stable 5, 6, 7-membered monocyclic or bicyclic or 10-membered bicyclic heterocyclic aromatic ring, and which consists of carbon atoms and from 1, 2, 3 or 4 cyclic heteroatoms independently selected from the group consisting of N, O and S. The nitrogen atom may be substituted or unsubstituted (i.e., N or NR, wherein R is H or other substituents already defined herein). The nitrogen and sulfur heteroatoms may optionally be oxidized (NO, and S(O)p, p represents 1 or 2). It is noted that the total number of S and O atoms in the aromatic heterocycle is not more than 1. Bridged rings are also included in the definition of heterocycle. A bridged ring forms when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. In bridged ring, the substituents recited for the ring may also be present on the bridge.

Examples of heterocyclic compounds include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidyl, phenanthridinyl, phenanthrolinyl, phenazinyl, phenothiazinyl, phenoxazinyl, benzoxanthinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolothienyl, thienooxazolyl, thienothiazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds.

The term "hydrocarbyl" or the specific term thereof (such as alkyl, alkenyl, alkynyl, aryl, and the like), by itself or as part of another substituent, means, unless specified otherwise, a straight or branched chain, or cyclic hydrocarbon radical, or combination thereof, which may be fully saturated (such as alkyl), mono- or polyunsaturated (such as alkenyl, alkynyl, aryl) and may be mono-, or poly-substituted, and may be monovalent (such as methyl), divalent (such as methylene), or multivalent (such as methenyl), and can include di- and multivalent radicals, having the number of carbon atoms designated (for example, $C_1$-$C_{12}$ means one to twelve carbons, $C_1$-$C_{12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_1$-$C_{12}$ is selected from $C_1$, $C_2$, $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic and aromatic hydrocarbon. The aliphatic hydrocarbon includes linear and cyclic hydrocarbon, which specifically includes, but is not limited to, alkyl, alkenyl, alkynyl. The aromatic hydrocarbon includes, but is not limited to, 6- to 12-membered aromatic hydrocarbon, such as phenyl, naphthyl, and the like. In some embodiments, the term "hydrocarbyl" means a straight or branched chain radical, or combination thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, isobutyl, cyclohexyl, (cyclohexyl)methyl, cyclopropylmethyl, homologs and isomers of, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, butenyl, crotyl, 2-isopentenyl, 2-(butadienyl), 2,4-pentadienyl, 3-(1, 4-pentadienyl), ethynyl, 1- and 3-propynyl, 3-butynyl, and higher homologs and isomers.

Unless specified otherwise, the term "heterohydrocarbyl" or the specific term thereof (such as heteroalkyl, heteroalkenyl, heteroalkynyl, heterophenyl, and the like), by itself or in combination with another term, means, a stable straight or branched chain, or cyclic hydrocarbon radical, or combinations thereof, consisting of a number of carbon atoms and at least one heteroatom. In some embodiments, the term "heteroalkyl", by itself or in combination with another term, means, a stable straight or branched chain, or cyclic hydrocarbon radical, or combinations thereof, consisting of a number of carbon atoms and at least one heteroatom. In a representative embodiment, the heteroatom is selected from the group consisting of B, O, N, and S, and wherein the nitrogen and sulfur atoms may optionally be oxidized and the nitrogen heteroatom may optionally be quaternized. The heteroatom or heteroatom radical may be placed at any interior position of the heteroalkyl group, including at the position at which the hydrocarbyl group is attached to the remainder of the molecule. But the terms "alkoxy", "alkylamino" and "alkylthio" (or thioalkoxy) are used in their conventional sense, and refers to those alkyl groups attached to the remainder of the molecule via an oxygen atom, an amino group or a sulfur atom, respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two heteroatoms may be consecutive, such as —$CH_2$—NH—$OCH_3$.

Unless specified otherwise, the terms "cyclohydrocarbyl" and "heterocyclohydrocarbyl" or the specific term thereof (such as aryl, heteroaryl, cycloalkyl, heterocycloalkyl, cycloalkenyl, heterocycloalkenyl, cycloalkynyl, heterocycloalkynyl, and the like), by themselves or in combination with other terms, represent, cyclic versions of "hydrocarbyl" and "heterohydrocarbyl", respectively. Additionally, for heterohydrocarbyl or heterocyclohydrocarbyl (such as heteroalkyl, heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Non-limiting examples of heterocyclic radicals include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran indole-3-yl, tetrahydrothien-2-yl, tetrahydrothien-3-yl, 1-piperazinyl, 2-piperazinyl, and the like.

Unless specified otherwise, the term "alkyl" is used to represent a linear or branched saturated hydrocarbyl which may be mono-substituted (such as —CH$_2$F) or poly-substituted (such as —CF$_3$), and may be monovalent (such as methyl), divalent (such as methylene), or multivalent (such as methyne). Examples of alkyl includes methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless specified otherwise, the term "alkenyl" refers to alkyl having one or more carbon-carbon double bonds which may occur in any point along the chain, which may be be mono-substituted or poly-substituted, and may be monovalent, divalent, or multivalent. Examples of alkenyl includes ethenyl, propenyl, butenyl, pentenyl, hexenyl, butadienyl, pentadienyl, dienyl and the like.

Unless specified otherwise, the term "alkynyl" refers to alkyl having one or more carbon-carbon triple bonds which may occur in any point along the chain, which may be be mono-substituted or poly-substituted, and may be monovalent, divalent, or multivalent. Examples of alkynyl includes ethynyl, propynyl, butynyl, pentynyl and the like.

Unless specified otherwise, cycloalkyl includes any stable cyclic or polycyclic hydrocarbyl, any of which is saturated, which may be be mono-substituted or poly-substituted, and may be monovalent, divalent, or multivalent. Examples of cycloalkyl includes, but not be limited to, cyclopropyl, norbornane, [2.2.2]bicyclooctane, [4.4.0]bicyclodecane and the like.

Unless specified otherwise, cycloalkenyl includes any stable cyclic or polycyclic hydrocarbyl which has one or more unsaturated carbon-carbon double bonds in any point of the ring, which may be be mono-substituted or poly-substituted, and may be monovalent, divalent, or multivalent. Examples of cycloalkenyl includes, but are not limited to, cyclopentenyl, cyclohexenyl and the like.

Unless specified otherwise, cycloalkynyl includes any stable cyclic or polycyclic hydrocarbyl which has one or more carbon-carbon triple bonds in any point of the ring, which may be be mono-substituted or poly-substituted, and may be monovalent, divalent, or multivalent.

The terms "halo" or "halogen", by themselves of as part of another substituent, mean, unless specified otherwise, a fluorine, chlorine, bromine, or iodine atom. Additionally, terms such as "haloalkyl", are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. Unless specified otherwise, examples of haloalkyl include, but are not limited to, trifluoromethyl, trichloromethyl, pentafluoroethyl, and pentachloroethyl.

"Alkoxy" represents an alkyl group as defined above with the indicated number of carbon atoms attached through an oxygen bridge, unless specified otherwise, $C_{1-6}$ alkoxy includes the alkoxy of $C_1$, $C_2$, $C_3$, $C_4$, $C_5$ and $C_6$. Examples of alkoxy include, but are not limited to, methoxy, ethoxy, n-propoxy, i-propoxy, n-butoxy, s-butoxy, t-butoxy, n-pentoxy, and s-pentoxy. The term "aryl" means, unless specified otherwise, a polyunsaturated, aromatic, hydrocarbon substituent, which may be mono-, di-, or poly-substituted, and may be monovalent, divalent, or multivalent, and which can be a single ring or multiple rings (such as 1 to 3 rings; wherein at least one ring is the aromatic which are fused together or linked covalently. The term "heteroaryl" refers to aryl groups (or rings) that contain from one to four heteroatoms. In one exemplary embodiment, the heteroatom is selected from B, N, O, and S, wherein the nitrogen and sulfur atoms are optionally oxidized, and the nitrogen atom (s) are optionally quaternized. A heteroaryl group can be attached to the remainder of the molecule through a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Unless specified otherwise, the term "aryl" when used in combination with other terms (e.g. aryloxy, arylthioxy, arylalkyl) includes both aryl and heteroaryl rings as defined above. Thus, the terms "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy) propyl, and the like).

The term "leaving group" means a functional group or atom which can be displaced by anther functional group or atom through a substitution reaction, such as a nucleophilic substitution reaction. By way of example, representative leaving groups include trifluoromethanesulfonate; chloro, bromo and iodo groups; sulfonic ester groups, such as mesylate, tosylate, brosylate, p-toluenesulfonate and the like; and acyloxy groups, such as acetoxy, trifluoroacetoxy and the like.

The term "protecting groups" include, but are not limited to "amino-protecting group", "hydroxyl-protecting group", and "thiol-protecting group". The term "amino-protecting group" means a protecting group suitable for preventing said reactions at N position of an amino group. Representative amino-protecting groups include, but not limited to, formyl; acyl, for example, alkane acyl, such as acetyl, trichloroacetyl or trifluoroacetyl; alkoxycarbonyl, such as tert-butoxycarbonyl (Boc); aryl methoxycarbonyl, such as benzyloxycarbonyl (Cbz), 9-fluorenylmethoxycarbonyl (Fmoc), aryl methyl, such as benzyl (Bn), trityl (Tr), 1,1-di(4'-methoxyphenyl) methyl; siliyl such as trimethylsilyl (TMS), tert-butyldimethylsilyl (TBS), and the like. The term "hydroxyl-protecting group" means a protecting group suitable for preventing said reactions at a carboxy group. Representative hydroxyl-protecting groups include, but are not limited to, alkyl, such as methyl, ethyl, and tert-butyl; acyl, for example, alkane acyl, such as acetyl; aryl methyl, such as benzyl (Bn), p-methoxybenzyl (PMB), 9-fluorenylmethyl (Fm), benzhydryl (diphenyl-methyl, DPM); siliyl, such as trimethylsilyl (TMS), tert-butyldimethylsilyl (TBS), and the like.

The compounds of the present invention can be prepared in a number of synthetic methods well known to one person skilled in the art. The methods includes the specific embodiments described below; the embodiments formed by the combination with the following embodiments and other chemical synthesis methods; and the substitution to the same methods well known to those skilled in the art. The preferred embodiments include, but are not limited to, the examples of the present invention.

The solvents used in the present invention are commercially available. And the following abbreviations are used in the present invention: aq represents water; HATU represents O-(7-azabenzotriazol-1-yl)-N,N,N',N'-tetramethyluronium hexafluoro phosphate, EDC represents N-(3-dimethylaminopropyl)-N'-ethylcarbodiimide hydrochloride; m-CPBA represents 3-chloroperoxybenzoic acid; eq represents equivalent, equal quantity; CDI represents carbonyl diimidazole; DCM represents dichloromethylene; PE represents petroleum ether; DIAD represents diisopropyl azodicarboxylate; DMF represents N, N-dimethylformamide; DMSO represents dimethyl sulfoxide; EtOAc represents ethyl acetate; EtOH represents ethanol; MeOH represents methanol; CBz represents benzyloxycarbonyl and is an amine-protecting group; BOC represents tert-butoxycarbonyl and is an amine-protecting group; HOAc represents acetic acid; NaCNBH$_3$ represents Sodium cyanoborohydride; r.t. represents room temperature; O/N represents overnight; THF represents tetrahydrofuran; Boc$_2$O represents di-t-butyldicarbonate; TFA represents trifluoroacetic acid; DIPEA represents diisopropylethylamine; SOCl$_2$ represents thionyl chloride, CS$_2$ represents carbon disulphide; TsOH represents p-toluenesulfonic acid; NFSI represents N-fluoro-N-(benzenesulfonyl) benzenesulfonamide; NCS represents 1-chloropyrrolidine-2,5-dione; n-Bu$_4$NF represents tetrabutylammonium fluoride; iPrOH represents 2-propanol; mp represents melting point; LDA represents Lithium diisopropylamide, Fmoc represents fluorenylmethoxycarbonyl, Alloc represents allyloxycarbonyl, Teco represents trimethylethoxycarbonyl, Pht represents o-phthalyl, Tos represents p-toluenesulfonyl, Tfa represents trifluoroacetyl, Bn represents benzyl, PMB represents p-methoxybenzyl.

The compounds are named by handwork or ChemDraw® software, and the commercially available compounds are used with the supplier catalog name.

DETAILED DESCRIPTION OF THE EMBODIMENTS

Example 1

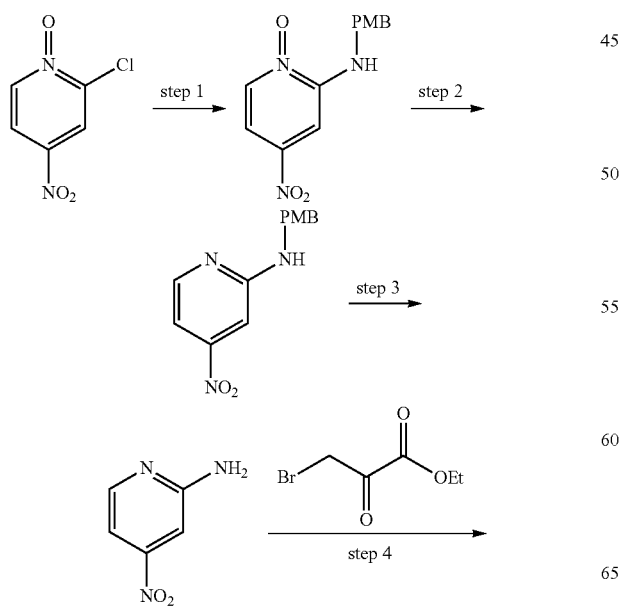

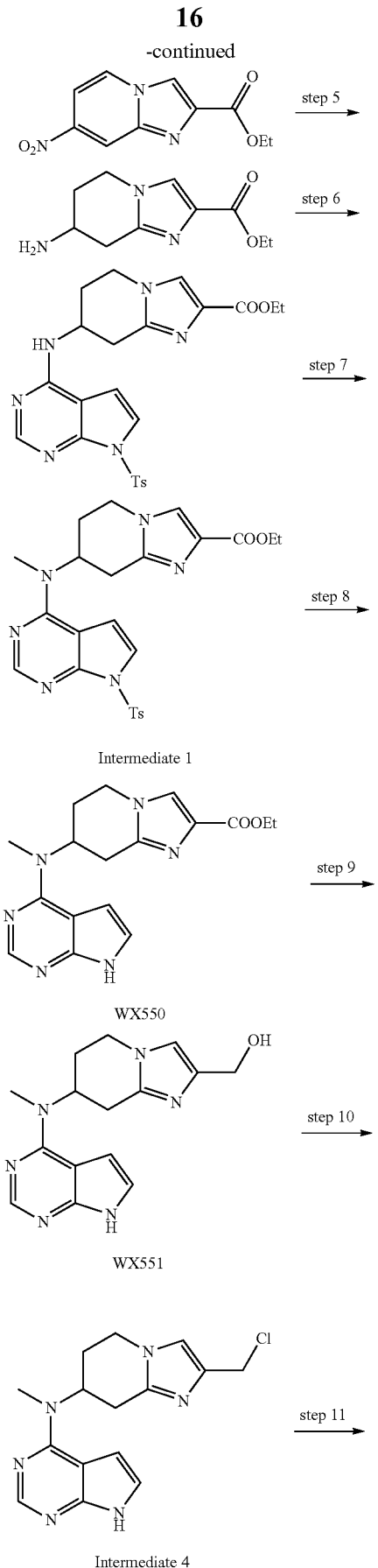

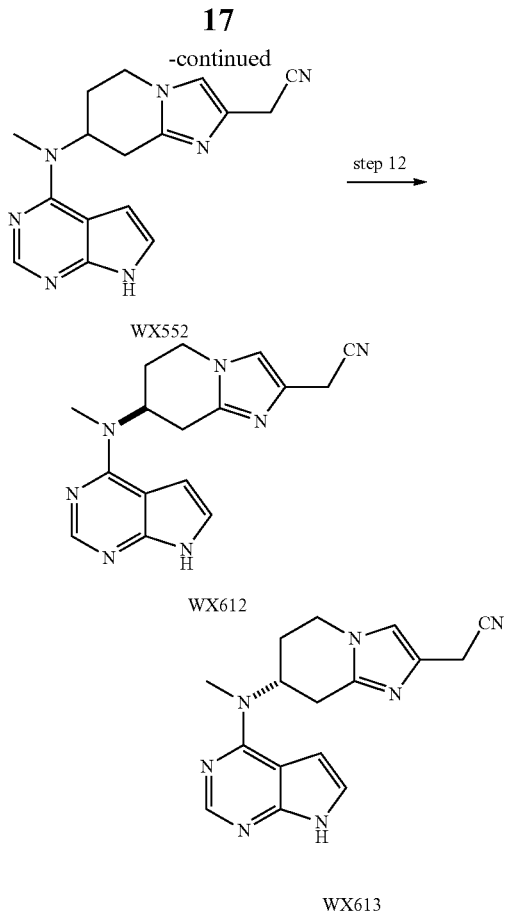

Step 1: 2-chloro-4-nitro-1-oxo-pyridin-1-ium (40.0 g, 229.2 mmol) and (methoxyphenyl) methanamine (63 g, 458.4 mmol) were dissolved in EtOH (400 mL). The resulting solution was stirred and refluxed for reacting for 5 hours. TLC (PE:EA=2:1) showed that the reaction was completed. Half of the volume of EtOH was concentrated and cooled in an ice bath for 2~3 hours. The cold mixture was filtered and the separated solid was washed with PE (60 mL×3) and ice water (60 mL×3) respectively, and then dried in vacuum to give N-[(4-(methoxyphenyl)methyl]-4-nitro-1-oxo-pyridin-1-ium-2-amine (38.6 g, 140.2 mmol, 61.2% yield) as an orange solid. MS (ESI) Calcd. for $C_{13}H_{13}N_3O_4$ 275, Found 276 $[M+H]^+$.

Step 2: To N-[(4-(methoxyphenyl)methyl]-4-nitro-1-oxo-pyridin-1-ium-2-amine (5.0 g, 18.16 mmol) in $CHCl_3$ (50 mL) was added dropwise $PCl_3$ (8.4 g, 60.8 mmol) at 0° C., after adding, the reaction mixture was warmed to 25° C. and stirred vigorously for 16 hours. TLC (PE:EA=1:1) showed that the reaction was completed. The reaction mixture was filtered and the resulting solid was washed with PE (30 mL×3) to give N-[(4-(methoxyphenyl)methyl]-4-nitro-pyridin-2-amine (4.2 g, a crude product) as a yellow solid, which was directly used in the next step without further purification. MS (ESI) Calcd. for $C_{15}H_{18}N_6$ 259, Found 260 $[M+H]^+$.

Step 3: To N-[(4-(methoxyphenyl)methyl]-4-nitro-pyridin-2-amine (4.2 g, 16.2 mmol) in toluene solution (10 mL) was added dropwise TFA (5.0 mL) at room temperature. Then, the mixture was stirred at 80° C. for reacting for 2 hours. TLC (PE:EA=1:1) showed that the reaction was completed. The mixture was concentrated under reduced pressure to remove the solvent. The residue was diluted with $H_2O$ (50 mL) and pH thereof was adjusted with solid $NaHCO_3$ to neutral. The water phase was extracted with EA (50 mL×3). The combined organic phase was dried with anhydrous sodium sulfate, filtered, and concentrated under reduced pressure. The resulting residue was purified through column chromatography (silicon dioxide, petroleum ether/ethyl acetate=1/0~1:1) to give 4-nitropyridin-2-amine (700 mg, 5.0 mmol, 31.1% yield) as an orange solid compound. MS (ESI) Calcd. for $C_5H_5N_3O_2$ 139, Found 140 $[M+H]^+$.

Step 4: To 4-nitropyridin-2-amine (200 mg, 1.4 mmol) in DME (5 mL) was added ethyl 3-bromo-2-oxopropanoate (280 mg, 1.4 mmol) at room temperature. After the resulting mixture was stirred at 25° C. for reacting for 1 hour, concentrated under reduced pressure to remove the solvent. The residue was dissolved with EtOH (10 mL) and refluxed for reacting for 3 hours. TLC showed that the reaction was completed. The reaction mixture was cooled to room temperature and the solvent was concentrated under reduced pressure. The residue was alkalified with saturated water solution of $NaHCO_3$ (25 mL). The water phase was extracted with DCM (15 mL×3). The combined organic phase was dried with anhydrous sodium sulfate, filtered, and concentrated under reduced pressure. The resulting residue was purified through rapid column chromatography (EA: PE=10-60%) to give ethyl 7-nitroimidazo[1,2-]pyridine-2-carboxylate (302 mg, 88.9% yield) as a pale yellow solid compound. MS (ESI) Calcd. for $C_{10}H_9N_3O_4$ 235, Found 236 $[M+H]^+$.

Step 5: To a solution of ethyl 7-nitroimidazo[1,2-]pyridine-2-carboxylate (150 mg, 637.8 mmol) in ethanol (20 mL) was added HCl (7 mg, 0.2 mmol) and $PtO_2$ (15 mg, 0.6 mmol) respectively at room temperature. The reaction system is vacuumed repeatedly and filled with nitrogen three times, and then filled with $H_2$ (50 psi) and stirred at 50° C. for reacting for 16 hours. TLC (PE:EA=1:1) showed that the reaction was completed. Half of the volume of the mixture was concentrated and filtered to give ethyl 7-amino-5,6,7,8-tetrahydroimidazo[1,2-α] pyridine-2-carboxylate hydrochloride (120 mg, crude product) as a white solid compound. MS (ESI) Calcd. for $C_{10}H_{15}N_3O_2$ 209, Found 210 $[M+H]^+$.

Step 6: Ethyl 7-amino-5,6,7,8-tetrahydroimidazo[1,2-a]pyridine-2-carboxylate hydrochloride (100 mg, 0.4 mmol) and 4-chloro-7-tosyl-pyrrolo[2,3-d]pyrimidine (137 mg, 0.4 mmol) was dissolved in n-BuOH (5 mL), and DIEA (158 mg, 1.2 mmol) was added. The resulting mixture was stirred and refluxed for reacting for 16 hours. LC-MS showed that the reaction was completed. The reaction mixture was concentrated under reduced pressure. The resulting residue was diluted with $H_2O$ (10 mL), the water phase was extracted with EA (20 mL×3). The combined organic phase was dried with anhydrous sodium sulfate, filtered, and concentrated under reduced pressure. The resulting residue was purified through preparative TLC (PE:EA=0:1) to give ethyl 7-[[7-tosyl-pyrrolo [2,3-d]pyrimidine-4-yl]amino]-5,6,7,8-tetrahydroimidazo[1,2-a]pyridine-2-carboxylate (55 mg, 0.11 mmol, 28.1% yield) as a pale yellow solid compound. MS (ESI) Calcd. for $C_{23}H_{24}N_6O_4S$ 480, Found 481 $[M+H]^+$.

Step 7: To a solution of ethyl 7-[[7-(tosyl)pyrrolo [2,3-d] pyrimidine-4-yl]amino]-5,6,7,8-tetrahydroimidazo[1,2-a]pyridine-2-carboxylate (3.0 g, 6.2 mmol) in THF (150 mL) was added NaH (499 mg, 12.5 mmol) in batches at 0° C. in $N_2$ atmosphere. The mixture was continued to stir at this temperature for 1 hour, and then MeI (7.1 g, 50.2 mmol) was added dropwise. After adding, it was moved to stir at room temperature for 1 hour. TLC showed that the reaction was completed. Saturated $NH_4Cl$ (10 mL) was added and quenched, and then ice water (50 mL) was added to dilute it. The water phase was extracted with a mixed solvent of DCM/MeOH (3:1, 50 mL×3). The combined organic phase was dried with anhydrous sodium sulfate, filtered, and concentrated under reduced pressure. The resulting crude product was purified through rapid column chromatography (DCM:MeOH=10:1) to give ethyl 7-[methyl-[7-(tosyl)pyrrolo[2,3-d]pyrimidine-4-yl]amino]-5,6,7,8-tetrahydroimidazo[1,2-a] pyridine-2-carboxylate (Intermediate 1) (1.5 g, 45% yield) as a pale yellow solid. MS (ESI) Calcd. for $C_{24}H_{26}N_6O_4S$ 494, Found 495 $[M+H]^+$.

Step 8: To a solution of ethyl 7-[methyl-[7-(tosyl)pyrrolo[2,3-d]pyrimidine-4-yl] amino]-5,6,7,8-tetrahydroimidazo[1,2-a]pyridine-2-carboxylate (1.5 g, 3.0 mmol) in EtOH (20 mL) was added NaOEt (1.0 g, 15 mmol) at 25° C., and stirred at this temperature for 16 hours. TLC (DCM:MeOH=10:1) showed that the reaction was completed. The reaction mixture was concentrated under reduced pressure. The residue was diluted with water (50 mL), and the water phase was extracted with DCM/MeOH (10:1, 50 mL×3). The combined organic phase was dried with anhydrous sodium sulfate, filtered, and concentrated under reduced pressure. The resulting residue was purified through column chromatography (silicon dioxide, DCM/MeOH=1/0~10:1) to give ethyl 7-[methyl(7H-pyrrolo[2,3-d]pyrimidine-4-yl)amino]-5,6,7,8-tetrahydroimidazo[1,2-a]pyridine-2-carboxylate (WX550, Intermediate 2) (600 mg, 1.76 mmol, 58.2% yield) as a white solid compound. MS (ESI) Calcd. for $C_{17}H_{20}N_6O_2$ 340, Found 341 $[M+H]^+$.

Step 9: To a solution of ethyl 7-[methyl(7H-pyrrolo[2,3-d]pyrimidine-4-yl)amino]-5,6,7,8-tetrahydroimidazo[1,2-a]pyridine-2-carboxylate (500 mg, 1.5 mmol) in THF (10.00 mL) was added LiAlH$_4$ (111 mg, 2.9 mmol) in batches at 0° C. The resulting mixture was moved to stir at room temperature for 2 hours. TLC (DCM:MeOH=10:1) showed that the reaction was completed. At 90° C., H$_2$O/THF=1/1 (20 mL) was added, quenched, and filtered. The water phase was extracted with DCM/MeOH (10:1, 50 mL×3). The combined organic phase was dried with anhydrous sodium sulfate, filtered, and concentrated under reduced pressure to give 7-[methyl(7H-pyrrolo[2,3-d]pyrimidine-4-yl)amino]-5,6,7,8-tetrahydroimidazo[1,2-a]pyridine-2-yl]methanol (Intermediate 3) (320 mg, crude product) as a pale yellow solid compound, which was directly used in the next step without further purification. MS (ESI) Calcd. for $C_{15}H_{18}N_6O$ 298, Found 299 $[M+H]^+$.

Step 10: To a solution of 7-[methyl(7H-pyrrolo[2,3-d]pyrimidine-4-yl)amino]-5,6,7,8-tetrahydroimidazo[1,2-a]pyridine-2-yl]methanol (150 mg, 0.5 mmol) in DCM (5 mL) was added thionyl chloride (300 mg, 2.5 mmol) at room temperature. The resulting mixture was stirred at 70° C. for 1 hour. TLC (DCM:MeOH=10:1) showed that the reaction was completed. The mixture was concentrated under reduced pressure to give N-[2-(chloromethyl)-5,6,7,8-tetrahydroimidazo[1,2-a]pyridine-7-yl]-N-methyl-7H-pyrrolo[2,3-d] pyrimidine-4-amine (150 mg, hydrochloride crude product) (Intermediate 4) as a crude product, which was directly used in the next step without further purification. MS (ESI) Calcd. for $C_{15}H_{17}ClN_6$ 316, Found 317 $[M+H]^+$.

Step 11: To a solution of N-[2-(chloromethyl)-5,6,7,8-tetrahydroimidazo[1,2-a] pyridine-7-yl]-N-methyl-7H-pyrrolo [2,3-d] pyrimidine-4-amine (150 mg, 0.42 mmol) in DMSO (5 mL) was added sodium cyanide (41 mg, 0.85 mmol). Then the mixture was stirred at 40° C. for reacting for 10 hours. LC-MS showed that the raw material was completely consumed and the product was produced. Water (10 mL) was added and quenched. The water phase was extracted with DCM/MeOH (3:1, 20 mL×3). The organic phase was combined, washed with saturated salt water (20 mL×2), dried with anhydrous sodium sulfate, filtered, and distilled under reduced pressure. The resulting residue was separated through preparative HPLC (alkaline condition) to give 2-[7-[methyl(7H-pyrrolo[2,3-d]pyrimidine-4-yl)amino]-5,6,7,8-tetrahydroimidazo[1,2-a]pyridine-2-yl]acetonitrile (WX552) (60 mg, 46% yield) as a white solid compound. MS (ESI) Calcd. for $C_{16}H_{17}N_7$ 307, Found 308 $[M+H]^+$. $^1$H NMR (400 MHz, DMSO-d$_6$) 8.12 (s, 1H), 7.16 (d, J=3.01 Hz, 1H), 7.02 (s, 1H), 6.61 (d, J=3.01 Hz, 1H), 4.11-4.22 (m, 1H), 3.95-4.08 (m, 1H), 3.79 (s, 2H), 3.28 (s, 3H), 2.88-3.08 (m, 2H), 2.26-2.41 (m, 1H), 2.05 (d, J=11.80 Hz, 1H).

Step 12: Racemic 2-[7-[methyl(7H-pyrrolo[2,3-d]pyrimidine-4-yl)amino]-5,6,7,8-tetrahydroimidazo[1,2-a]pyridine-2-yl]acetonitrile (WX552) (30 mg) was separated through chiral column to give (S or R) 2-[7-[methyl(7H-pyrrolo[2,3-d]pyrimidine-4-yl) amino]-5,6,7,8-tetrahydroimidazo[1,2-a]pyridine-2-yl]acetonitrile (WX612, 10 mg) and (R or S)$_2$-[7-[methyl(7H-pyrrolo[2,3-d]pyrimidine-4-yl)amino]-5,6,7,8-tetrahydroimidazo [1,2-a]pyridine-2-yl]acetonitrile (WX613, 11 mg).

The condition of SFC separation:
Column: AD (250 mm×30 mm, 10 um) chiral column
Mobile phase: A: supercritical CO$_2$, B: B: isopropanol (containing 0.1% of ammonia water), A:B=60:40
Flow rate: 80 mL/min
Column temperature: 38° C.
Wavelength: 220 nm
Injection pressure: 100 Bar
Nozzle temperature: 60° C.
Evaporating temperature: 20° C.
Finishing temperature: 25° C.

WX612: retention time 4.870 min; MS (ESI) Calcd. for $C_{16}H_{17}N_7$ 307, Found 308 $[M+H]^+$. $^1$H NMR (400 MHz, METHANOL-d$_4$) 8.15 (s, 1H), 7.14 (d, J=3.51 Hz, 1H), 7.05 (s, 1H), 6.71 (d, J=3.51 Hz, 1H), 5.41-5.51 (m, 1H), 4.23-4.30 (m, 1H), 4.14 (dt, J=4.27, 12.17 Hz, 1H), 3.77 (s, 2H), 3.40 (s, 3H), 3.04-3.19 (m, 2H), 2.46 (dq, J=5.77, 12.38 Hz, 1H), 2.21 (d, J=13.05 Hz, 1H).

WX613: retention time 5.709 min; MS (ESI) Calcd. for $C_{16}H_{17}N_7$ 307, Found 308 $[M+H]^+$. $^1$H NMR (400 MHz, METHANOL-d$_4$) 8.15 (s, 1H), 7.14 (d, J=3.51 Hz, 1H), 7.04 (s, 1H), 6.70 (d, J=3.51 Hz, 1H), 5.37-5.51 (m, 1H), 4.22-4.31 (m, 1H), 4.14 (dt, J=4.52, 12.30 Hz, 1H), 3.77 (s, 2H), 3.40 (s, 3H), 3.03-3.20 (m, 2H), 2.46 (dq, J=5.90, 12.34 Hz, 1H), 2.21 (d, J=11.80 Hz, 1H)

Example 2

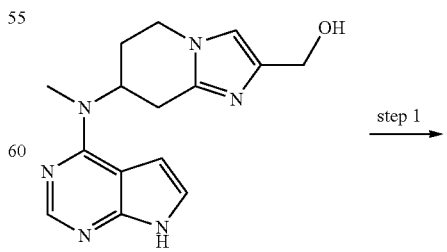

WX551 step 1

21
-continued

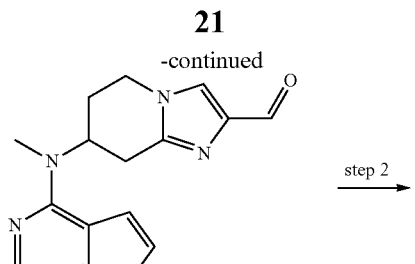

step 2 →

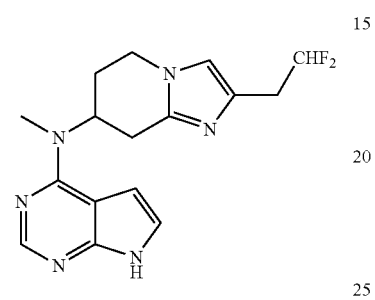

WX611

22
Example 3

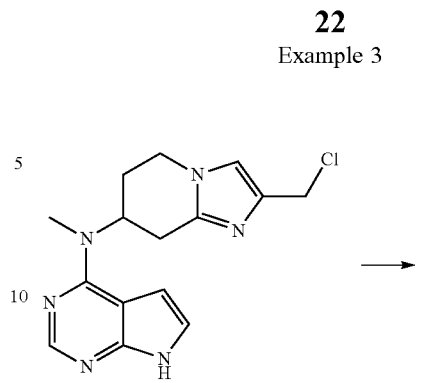

Intermediate 4

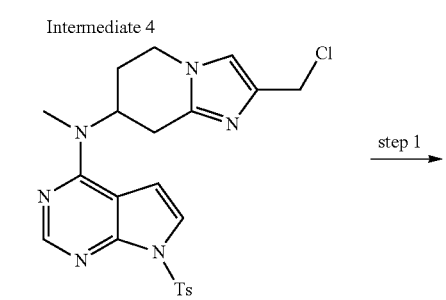

step 1 →

Intermediate 5

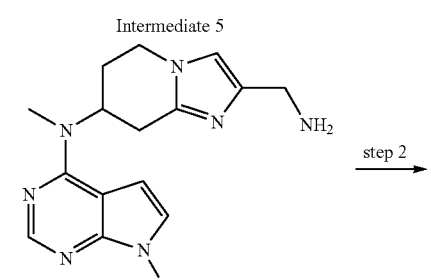

step 2 →

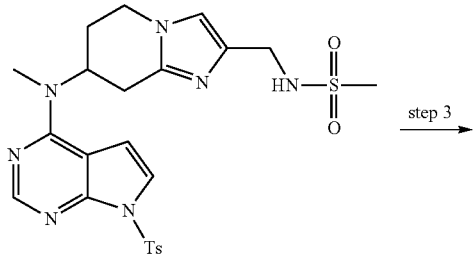

step 3 →

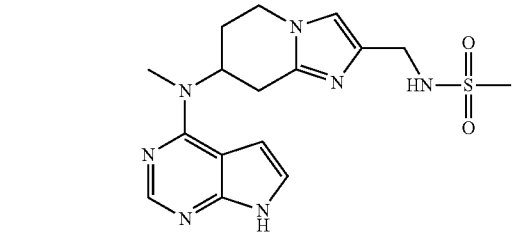

WX606

Step 1: To a solution of 7-[methyl(7H-pyrrolo[2,3-d]pyrimidine-4-yl)amino]-5,6,7,8-tetrahydroimidazo[1,2-a]pyridine-2-yl]methanol (Intermediate 2) (200 mg, 0.44 mmol) in DCM (20 mL) was added activated manganese dioxide (384 mg, 4.4 mmol) at room temperature. The resulting suspension was stirred at 50° C. for reacting for 4 hours. LC-MS showed that the reactant was completely consumed. The reaction mixture was cooled to room temperature, filtered, and concentrated to give 7-[methyl(7H-pyrrolo [2,3-d]pyrimidine-4-yl)amino]-5,6,7,8-tetrahydroimidazo[1,2-a]pyridine-2-carbaldehyde (160 mg, crude product) as a white solid, which was directly used in the next step without further purification. MS (ESI) Calcd. for $C_{15}H_{16}N_6O$ 296, Found 297 [M+H]$^+$.

Step 2: To a solution of 7-[methyl(7H-pyrrolo [2,3-d]pyrimidine-4-yl)amino]-5,6,7,8-tetrahydroimidazo[1,2-a]pyridine-2-carbaldehyde (159 mg, 0.35 mmol) in DCM (8 mL) was added diethylaminosulfur trifluoride (DAST) (228 mg, 1.41 mmol) at 0° C. in nitrogen atmosphere. After adding, the mixture was moved to stir at 25° C. for reacting for 14 hours. LC-MS showed that the reaction was completed. The reaction mixture was poured into cooling saturated sodium bicarbonate solution (10 mL), and the water phase was extracted with DCM/MeOH (10:1, 15 mL×3). The combined organic phase was washed with saturated salt water, dried with anhydrous sodium sulfate, filtered, and distilled under reduced pressure. The resulting residue was purified through preparative HPLC (alkaline method) to give N-(2-(difluoromethyl)-5,6,7,8-tetrahydroimidazo[1,2-a]pyridine-7-yl)-N-methyl-7H-pyrrolo[2,3-d]pyrimidine-4-amino(WX611) (156 mg, 93.6% yield). MS (ESI) Calcd. for $C_{16}H_{18}F_2N_6$ 332, Found 333 [M+H]$^+$. $^1$H NMR (400 MHz, METHANOL-$d_4$) 8.44 (br. s., 1H), 8.01 (br. s., 1H), 7.40 (br. s., 1H), 7.03 (br. s., 1H), 5.84-6.22 (m, 1H), 5.64 (br. s., 1H), 4.55 (d, J=9.79 Hz, 1H), 4.40 (d, J=10.29 Hz, 1H), 3.78 (t, J=14.43 Hz, 2H), 3.56 (br. s., 3H), 3.48 (br. s., 2H), 3.37 (s, 1H), 2.68 (d, J=7.53 Hz, 1H), 2.42 (d, J=12.30 Hz, 1H)

Step 1: To a solution of N-[2-(chloromethyl)-5,6,7,8-tetrahydroimidazo[1,2-a]pyridine-7-yl]-N-methyl-7-(p-toluenesulfonyl)pyrrolo[2,3-d]pyrimidine-4-amine (Intermediate 5) (130 mg, 0.28 mmol) in pyridine (5 mL) was added a solution of $NH_3$ in MeOH (10 mL, 10M) at room temperature. The resulting mixture was stirred at 25° C. for 10 hours. TLC (DCM:MeOH=10:1) showed that the reaction was completed. H₂O (20 mL) was added to quench the mixture. The water phase was extracted with DCM/MeOH (5:1, 15 mL×3). The combined organic phase was washed with saturated salt water, dried with anhydrous sodium sulfate, filtered, and concentrated under reduced pressure to give N-[2-(aminomethyl)-5,6,7,8-tetrahydroimidazo[1,2-a]pyridine-7-yl]-N-methyl-7-(p-toluenesulfonyl)pyrrolo[2,3-d]pyrimidine-4-amine (60 mg, crude product) as a yellow solid compound, which was directly used in the next step without further purification. MS (ESI) Calcd. for C₂₂H₂₅N₇O₂S 451, Found 452 [M+H]⁺.

Step 2: To a solution of N-[2-(aminomethyl)-5,6,7,8-tetrahydroimidazo[1,2-a] pyridine-7-yl]-N-methyl-7-(p-toluenesulfonyl)pyrrolo[2,3-d]pyrimidine-4-amine (150 mg, 0.33 mmol) and TEA (100 mg, 1 mmol) dissolved in DCM (5 mL), was added methylsulfonyl chloride (46 mg, 0.4 mmol) at 0° C. The resulting mixture was moved to 25° C. for stirring for 16 hours. LC-MS showed that the reaction was completed. The mixture was concentrated under reduced pressure to remove the solvent. The resulting residue was dissolved with H₂O (15 mL) and extracted with DCM/MeOH (5:1, 30 mL×3). The combined organic phase was dried with anhydrous sodium sulfate, filtered, and concentrated under reduced pressure to give N-((7-(methyl-(7-p-toluoyl-7H-pyrrolo[2,3-d]pyrimidine-4-yl)amine)-5,6,7,8-tetrahydroimidazo[1,2-a]pyridine-2-yl)methyl)methanesulfonamide (60 mg, crude product) as a pale yellow solid compound, which was directly used in the next step without further purification. MS (ESI) Calcd. for C₂₃H₂₇N₇O₄S₂ 529, Found 530 [M+H]⁺.

Step 3: To a solution of N-((7-(methyl-(7-p-toluoyl-7H-pyrrolo[2,3-d]pyrimidine-4-yl) amine)-5,6,7,8-tetrahydroimidazo[1,2-a]pyridine-2-yl)methyl)methanesulfonamide (50 mg, 0.94 mmol) in H₂O (5 mL)/THF (5 mL) was added NaOH (6 mg, 0.14 mmol) at room temperature. The resulting mixture was stirred and refluxed at 90° C. for 4 hours. TLC showed that the raw material was completely consumed and a new point was produced; LCMS showed the target molecular weight. The reaction mixture was concentrated under reduced pressure to remove the solvent. The residue was dissolved with H₂O (15 mL) and extracted with dichloromethane/isopropanol (3:1, 20 mL×3). The combined organic phase was dried with anhydrous sodium sulfate, filtered, and concentrated under reduced pressure. The resulting residue was purified through preparative HPLC (alkaline condition) to give N-((7-(methyl-(7H-pyrrolo[2,3-d]pyrimidine-4-yl)amine)-5,6,7,8-tetrahydroimidazo[1,2-a]pyridine-2-yl)methyl)methanesulfonamide (WX606.22 mg, 62.1% yield). MS (ESI) Calcd. for C₁₆H₂₁N₇O₂S 375, Found 376 [M+H]⁺. ¹H NMR (400 MHz, METHANOL-d₄) 8.15 (s, 1H), 7.13 (d, J=3.51 Hz, 1H), 7.01 (s, 1H), 6.70 (d, J=3.76 Hz, 1H), 5.39-5.48 (m, 1H), 4.22-4.29 (m, 1H), 4.17 (s, 3H), 3.40 (s, 3H), 3.04-3.14 (m, 2H), 2.91 (s, 3H), 2.45 (dq, J=5.90, 12.34 Hz, 1H), 2.21 (d, J=11.29 Hz, 1H)

Example 4

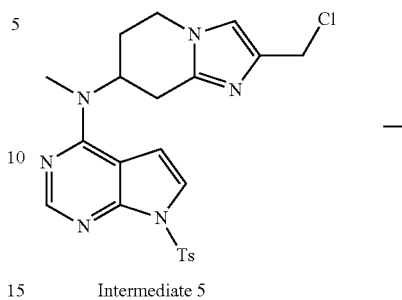

The method of preparation and purification for N-methyl-N-[2-(methylaminomethyl)-5,6,7,8-tetrahydroimidazo[1,2-a]pyridine-7-yl]-7H-7H-pyrrolo[2,3-d]pyrimidine-4-amine (WX605) is similar to the method of preparation and purification for WX606. To a solution of N-[2-(chloromethyl)-5,6,7,8-tetrahydroimidazo[1,2-a]pyridine-7-yl]-N-methyl-7-(p-toluenesulfonyl)pyrrolo[2,3-d]pyrimidine-4-amine (Intermediate 5) (130 mg, 0.28 mmol) in pyridine (5 mL) was added a solution of methylamine in MeOH (10 mL, 10M) to give methylamine compound, which was hydrolyzed with NaOH in H₂O (5 mL)/THF (5 mL). After completed reaction, it was treated with same process and separated through HPLC to give N-methyl-N-[2-(methylaminomethyl)-5,6,7,8-tetrahydroimidazo[1,2-a] pyridine-7-yl]-7H-7H-pyrrolo[2,3-d]pyrimidine-4-amine (WX605) (25 mg, 68% yield). MS (ESI) Calcd. for C₁₆H₂₁N₇ 311, Found 312 [M+H]⁺. ¹H NMR (400 MHz, CHLOROFORM-d) 8.15 (s, 1H), 7.02 (d, J=3.51 Hz, 1H), 6.83 (s, 1H), 6.54 (d, J=3.51 Hz, 1H), 5.46 (br. s., 1H), 4.00-4.18 (m, 2H), 3.67 (s, 2H), 3.37 (d, J=16.31 Hz, 2H), 3.32 (s, 3H), 3.08-3.19 (m, 1H), 2.96 (dd, J=11.80, 16.06 Hz, 1H), 2.44 (s, 3H)

Example 5

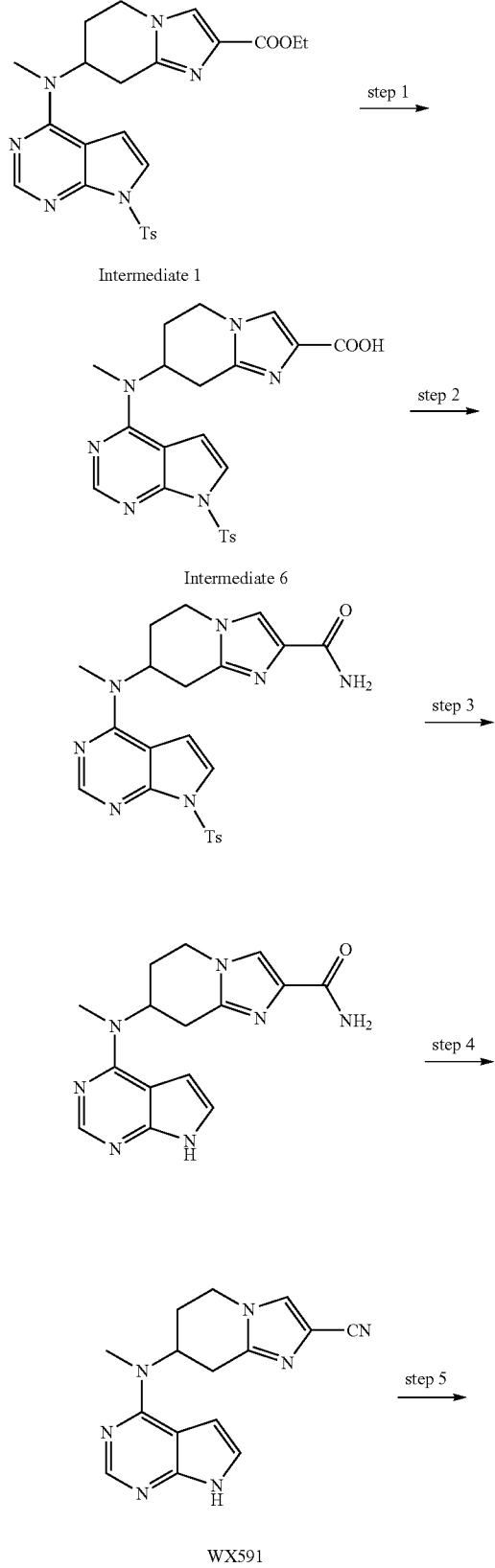

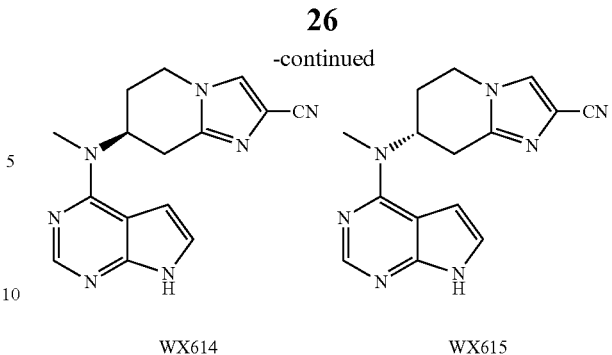

Step 1: To a solution of methyl ethyl 7-[methyl-[7-(tosyl) pyrrolo[2,3-d]pyrimidine-4-yl]amino]-5,6,7,8-tetrahydroimidazo[1,2-a]pyridine-2-carboxylate (4.0 g, 8.1 mmol) in TH (40 mL) and $H_2$ (8 mL) was added $LiOH.H_2O$ (509 mg, 12.1 mmol). The mixture was stirred at 20° C. for 10 hours. TLC showed that the reactant was completely consumed. THF was removed from the reaction mixture under reduced pressure. The residue was adjusted with 2M HCl (4 mL) to pH=2-3 to give a white solid. The solid was filtered out and concentrated under reduced pressure to give 7-[methyl-[7-(tosyl) pyrrolo[2,3-d]pyrimidine-4-yl]amino]-5,6,7,8-tetrahydroimidazo[1,2-a]pyridine-2-carboxylic acid (3.6 g, 95.4% yield) as a white solid. MS (ESI) Calcd. for $C_{22}H_{22}N_6O_4S$ 466, Found 467 $[M+H]^+$.

Step 2: To a solution of 7-[methyl-[7-(tosyl)pyrrolo[2,3-d]pyrimidine-4-yl]amino]-5,6,7,8-tetrahydroimidazo[1,2-a]pyridine-2-carboxylic acid (1.8 g, 3.9 mmol) in DMF (20 mL) was added CDI (751 mg, 4.6 mmol) at 0° C. The temperature of the reaction mixture was warmed to 25° C. to stir for 2 hours. After solid ammonium chloride (2.1 g, 38.6 mmol) was added, the reaction was carried out at room temperature overnight. LC-MS showed that the reactant was completely consumed. The reaction mixture was poured into ice water (50 mL) and white solid was separated out. The solid was filtered, washed with water (20 mL), and spun dry to give 7-[methyl-[7-(tosyl)pyrrolo[2,3-d] pyrimidine-4-yl] amino]-5,6,7,8-tetrahydroimidazo[1,2-a]pyridine-2-carboxamide (2.5 g, crude product) as a white solid, which was directly used in the next step. MS (ESI) Calcd. for $C_{22}H_{23}N_7O_3S$ 465, Found 466 $[M+H]^+$.

Step 3: 7-[methyl-[7-(tosyl)pyrrolo[2,3-d]pyrimidine-4-yl]amino]-5,6,7,8-tetrahydroimidazo [1,2-a]pyridine-2-carboxamide (2.5 g, 5.4 mmol) was dissolved in THF (20 mL), MeOH (10 mL) and $H_2O$ (6 mL), and NaOH (429.6 mg, 10.7 mmol) was added. The mixture was heated to 60° C. and stirred for 30 min. LC-MS showed that the reactant was completely consumed. The reaction mixture was concentrated under reduced pressure to give 7-[methyl-[7 hydropyrrolo[2,3-d]pyrimidine-4-yl]amino]-5,6,7,8-tetrahydroimidazo [1,2-a]pyridine-2-carboxamide (2.0 g crude product) as a white solid, which was directly used in the next step. MS (ESI) Calcd. for $C_{15}H_{17}N_7O$ 311, Found 312 $[M+H]^+$.

Step 4: To a solution of 7-[methyl-[7 hydropyrrolo[2,3-d]pyrimidine-4-yl]amino]-5,6,7,8-tetrahydroimidazo [1,2-a] pyridine-2-carboxamide (2.0 g, 6.4 mmol) and triethylamine (3.9 g, 38.5 mmol) in THF (20 mL) was added dropwise TFAA (4.1 g, 19.3 mmol) at 0° C. After adding, the reaction mixture was stirred at room temperature for 30 min. LC-MS showed that the reactant was completely consumed. The reaction mixture was poured into ice water (20 mL) and extracted with DCM/MeOH (5:1, 100 mL×2). The combined organic phase was washed with saturated salt water (20 mL), dried with anhydrous sodium sulfate, filtered, and concentrated under reduced pressure to give the residue. The residue was purified through column chromatography (DCM/MeOH=40/1 to 20:1) to give 7-[methyl-[7 hydropyrrolo[2,3-d]pyrimidine-4-yl]amino]-5,6,7,8-tetrahydroimidazo [1,2-a]pyridine-2-nitrile (WX591, 378 mg, 19.8% yield). MS (ESI) Calcd. for $C_{15}H_{15}N_7$ 293, Found 294 [M+H]$^+$. 1H NMR (400 MHz, DMSO-d6) 11.44-11.71 (m, 1H), 7.99-8.17 (m, 2H), 7.11-7.20 (m, 1H), 6.63 (dd, J=1.76, 3.26 Hz, 1H), 5.33 (br. s., 1H), 4.21-4.31 (m, 1H), 4.13 (dt, J=4.14, 12.49 Hz, 1H), 3.27 (s, 3H), 2.91-3.11 (m, 2H), 2.31-2.44 (m, 1H), 2.07 (d, J=11.54 Hz, 1H).

Step 5: Racemic 7-[methyl-[7 hydropyrrolo[2,3-d]pyrimidine-4-yl]amino]-5,6,7,8-tetrahydroimidazo [1,2-a]pyridine-2-nitrile (30 mg, 102.3 umol) was separated through chiral column to give (S or R) 7-[methyl-[7 hydropyrrolo[2,3-d]pyrimidine-4-yl]amino]-5,6,7,8-tetrahydroimidazo [1,2-a]pyridine-2-nitrile (P1, WX614, 10 mg, 32.8% yield) and (R or S) 7-[methyl-[7 hydropyrrolo[2,3-d]pyrimidine-4-yl]amino]-5,6,7,8-tetrahydroimidazo [1,2-a]pyridine-2-nitrile (WX615, 10 mg, 31.9% yield).

The condition of SFC separation:
Column: AD (250 mm×30 mm, 10 um) chiral column
Mobile phase: A: supercritical $CO_2$, B: B: ethanol (containing 0.1% of isopropanol),
A:B=55:45
Flow rate: 80 mL/min
Column temperature: 38° C.
Wavelength: 220 nm
Injection pressure: 100 Bar
Nozzle temperature: 60° C.
Evaporating temperature: 20° C.
Finishing temperature: 25° C.
WX614: retention time 5.507 min; MS (ESI) Calcd. for $C_{15}H_{15}N_7$ 293, Found 294 [M+H]$^+$. 1H NMR (400 MHz, DMSO-d6) 11.44-11.71 (m, 1H), 7.99-8.17 (m, 2H), 7.11-7.20 (m, 1H), 6.63 (dd, J=1.76, 3.26 Hz, 1H), 5.33 (br. s., 1H), 4.21-4.31 (m, 1H), 4.13 (dt, J=4.14, 12.49 Hz, 1H), 3.27 (s, 3H), 2.91-3.11 (m, 2H), 2.31-2.44 (m, 1H), 2.07 (d, J=11.54 Hz, 1H).
WX615: retention time 6.407 min; MS (ESI) Calcd. for $C_{15}H_{15}N_7$ 293, Found 294 [M+H]$^+$. 1H NMR (400 MHz, DMSO-d6) 11.44-11.71 (m, 1H), 7.99-8.17 (m, 2H), 7.11-7.20 (m, 1H), 6.63 (dd, J=1.76, 3.26 Hz, 1H), 5.33 (br. s., 1H), 4.21-4.31 (m, 1H), 4.13 (dt, J=4.14, 12.49 Hz, 1H), 3.27 (s, 3H), 2.91-3.11 (m, 2H), 2.31-2.44 (m, 1H), 2.07 (d, J=11.54 Hz, 1H).

Example 6

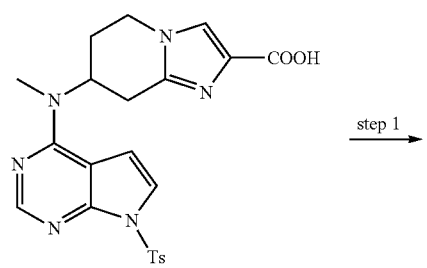

Intermediate 6

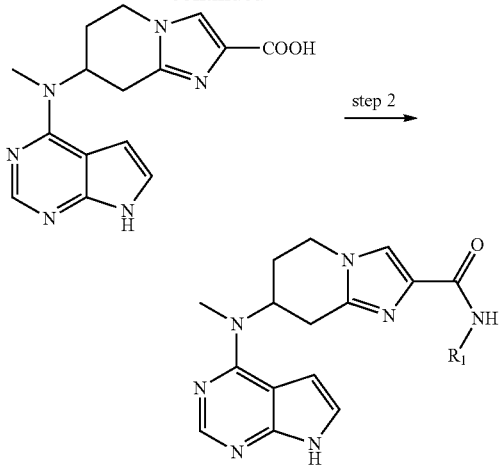

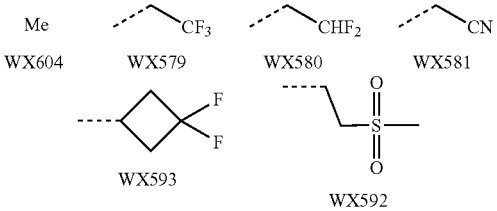

Step 2: The method of preparation and purification for 7-[methyl(7H-pyrrolomid[2,3-d]pyrimidine-4-yl]amino]-5,6,7,8-tetrahydroimidazo[1,2-a]pyridine-2-carboxylic acid is similar to the method of preparation and purification for 7-[methyl-[7 hydropyrrolo[2,3-d] pyrimidine-4-yl]amino]-5,6,7,8-tetrahydroimidazo [1,2-a]pyridine-2-carboxamide. MS (ESI) Calcd. for $C_{15}H_{16}N_6O_2$ 312, Found 313 [M+H]$^+$.

Step 2: 7-[methyl(7H-pyrrolo[2,3-d]pyrimidine-4-yl]amino]-5,6,7,8-tetrahydroimidazo [1,2-a]pyridine-2-carboxylic acid (120 mg, 384.2 umol) and EDCI (184 mg, 960.5 umol) was dissolved in pyridine (5 mL). The reaction mixture was stirred at 25° C. for 15 min, and then 3,3-difluorocyclobutanamine (120 mg, 384.2 umol) was added. The mixture was stirred at 25° C. for 1 hour. LC-MS showed that the raw material was completely consumed. The reaction mixture was diluted with water (20 mL), and extracted with DCM:i-PrOH=3:1(20 mL×3). The combined organic layer was dried with anhydrous sodium sulfate, filtered, and concentrated under reduced pressure to give the residue. The resulting residue was purified through preparative HPLC (alkaline condition) to give N-(3,3-difluorocyclobutyl)-7-[methyl(7H-pyrrolo[2,3-d]pyrimidine-4-yl]amino]-5,6,7,8-tetrahydroimidazo [1,2-a]pyridine-2-carboxamide (WX593) (30 mg, 15.9% yield). MS (ESI) Calcd. for $C_{19}H_{21}F_2N_7O$ 401, Found 402 [M+H]$^+$. $^1$H NMR (400 MHz, METHANOL-d$_4$) 8.15 (s, 1H), 7.61 (s, 1H), 7.14 (d, J=3.76 Hz, 1H), 6.71 (d, J=3.51 Hz, 1H), 5.42-5.53 (m, 1H), 4.30-4.39 (m, 2H), 4.14-4.27 (m, 1H), 3.41 (s, 3H), 3.08-3.23 (m, 2H), 2.91-3.05 (m, 2H), 2.62-2.78 (m, 2H), 2.48 (dq, J=5.65, 12.34 Hz, 1H), 2.23 (d, J=11.29 Hz, 1H)

The Compounds WX579, WX580, WX581, WX592 and WX604 can be produced through method of preparation and purification similar to Compound WX593. WX593 (15 mg, 9.6% yield). MS (ESI) Calcd. for $C_{17}H_8F_3N_7O$ 393, Found 394 [M+H]$^+$. $^1$H NMR (400 MHz, METHANOL-d$_4$) 8.15

(s, 1H), 7.66 (s, 1H), 7.14 (d, J=3.51 Hz, 1H), 6.71 (d, J=3.51 Hz, 1H), 5.41-5.54 (m, 1H), 4.28-4.39 (m, 1H), 4.20 (dt, J=4.39, 12.36 Hz, 1H), 4.03-4.13 (m, 2H), 3.40 (s, 3H), 3.08-3.23 (m, 2H), 2.47 (dq, J=5.77, 12.38 Hz, 1H), 2.23 (d, J=11.54 Hz, 1H)

WX580 (25 mg, 29.7% yield). MS (ESI) Calcd. for $C_{17}H_{19}F_2N_7O$ 375, Found 376 [M+H]$^+$. $^1$H NMR (400 MHz, METHANOL-$d_4$) 8.44 (br. s., 1H), 8.01 (br. s., 1H), 7.40 (br. s., 1H), 7.03 (br. s., 1H), 5.84-6.22 (m, 1H), 5.64 (br. s., 1H), 4.55 (d, J=9.79 Hz, 1H), 4.40 (d, J=10.29 Hz, 1H), 3.78 (t, J=14.43 Hz, 2H), 3.56 (br. s., 3H), 3.48 (br. s., 2H), 3.37 (s, 1H), 2.68 (d, J=7.53 Hz, 1H), 2.42 (d, J=12.30 Hz, 1H)

WX581 (35 mg, 44.6% yield). MS (ESI) Calcd. for $C_{17}H_{18}N_8O$ 350, Found 351 [M+H]$^+$. $^1$H NMR (400 MHz, METHANOL-$d_4$) 8.15 (s, 1H), 7.67 (s, 1H), 7.14 (d, J=3.76 Hz, 1H), 6.71 (d, J=3.51 Hz, 1H), 5.42-5.55 (m, 1H), 4.30-4.40 (m, 3H), 4.21 (dt, J=4.52, 12.42 Hz, 1H), 3.41 (s, 3H), 3.08-3.23 (m, 2H), 2.48 (tt, J=6.24, 12.45 Hz, 1H), 2.23 (d, J=10.29 Hz, 1H)

WX592 (25 mg, 15.6% yield). MS (ESI) Calcd. for $C_{18}H_{23}N_7O_3S$ 417, Found 418 [M+H]$^+$. $^1$H NMR (400 MHz, METHANOL-$d_4$) 8.44 (s, 1H), 7.95 (s, 1H), 7.41 (d, J=3.51 Hz, 1H), 7.04 (d, J=3.76 Hz, 1H), 5.64 (d, J=8.53 Hz, 1H), 4.55 (dd, J=4.02, 13.30 Hz, 1H), 4.37 (dt, J=4.27, 12.55 Hz, 1H), 3.88 (t, J=6.65 Hz, 2H), 3.56 (s, 3H), 3.42-3.49 (m, 4H), 3.05 (s, 3H), 2.59-2.74 (m, 1H), 2.42 (d, J=13.05 Hz, 1H)

WX604 (65 mg, 41.6% yield). MS (ESI) Calcd. for $C_{16}H_{19}N_7O$ 325, Found 326 [M+H]$^+$. $^1$H NMR (400 MHz, CHLOROFORM-d) 8.13 (s, 1H), 7.45 (s, 1H), 7.02 (d, J=3.51 Hz, 1H), 6.52 (d, J=3.51 Hz, 1H), 5.45 (br. s., 1H), 4.06-4.25 (m, 2H), 4.02 (br. s., 2H), 3.26-3.36 (m, 4H), 3.07-3.19 (m, 1H), 2.96 (dd, J=11.80, 16.06 Hz, 1H), 2.09-2.37 (m, 2H)

Test for in vitro activity of Jak1, Jak2, and Jak3 Kinase

Experimental Materials

Recombinant human protease of JAK1, JAK2 and JAK3 were purchased from Life technology. LANCE Ultra ULight™-JAK-1 (Tyr1023) peptide and LANCE Eu-W1024 Anti-phosphotyrosine (PT66) were purchased from PerkinElmer. Multimode ELISA, Envison(PerkinElmer) reader was used.

Experimental Method

The test compound was diluted according to gradient of three times concentration with a final concentration of from 10 uM to 0.17 nM at 11 concentrations totally, each concentration with two complex holes, and the content of DMSO in the detection was 1%.

Enzyme Reaction of JAK1

2 nM of JAK1 Protein kinase, 50 nM of LANCE Ultra ULight™-JAK-1(Tyr1023) peptide, 38 uM of ATP, 50 mM of HEPES (pH 7.5), 10 mM of $MgCl_2$, 1 mM of EGTA, 2 mM of DTT, 0.01% BRIJ-35. Checker board is White Proxiplate 384-Plus plate (PerkinElmer). The reaction was carried out at room temperature for 90 min and the reaction system was 10 ul.

Enzyme Reaction of JAK2

0.02 nM of JAK2 Protein kinase, 50 nM of LANCE Ultra ULight™-JAK-1(Tyr1023) peptide, 12 uM of ATP, 50 mM of HEPES (pH 7.5), 10 mM of $MgCl_2$, 1 mM of EGTA, 2 mM of DTT, 0.01% BRIJ-35. Checker board is White Proxiplate 384-Plus plate (PerkinElmer). The reaction was carried out at room temperature for 60 min and the reaction system was 10 ul.

Enzyme Reaction of JAK3

0.05 nM of JAK2 Protein kinase, 50 nM of LANCE Ultra ULight™-JAK-1(Tyr1023) peptide, 4 uM of ATP, 50 mM of HEPES (pH 7.5), 10 mM of $MgCl_2$, 1 mM of EGTA, 2 mM of DTT, 0.01% BRIJ-35. Checker board is White Proxiplate 384-Plus plate (PerkinElmer). The reaction was carried out at room temperature for 90 min and the reaction system was 10 ul.

Determination for Reaction 10 ul detection reagent was added to reaction plate, wherein the final concentration of LANCE Eu-W1024 Anti-phosphotyrosine (PT66) was 2 nM, the final concentration of EDTA was 10 nM, incubated at room temperature for 60 min, with Envison reader.

Data Analysis

The reading was converted to inhibition ratio (%) by the following formula: the inhibition ratio (%)=(Min−Ratio)/(Max−Min)×100%. Four parameter curve fitting (Model 205 in XLFIT5, iDBS) measured IC50 data, as shown in Table 1.

TABLE 1

| Compound | JAK1 | JAK2 |
|---|---|---|
| WX550 | C | D |
| WX551 | C | D |
| WX552 | B | C |
| WX579 | C | D |
| WX580 | C | D |
| WX581 | C | D |
| WX593 | D | D |
| WX592 | D | D |
| WX604 | C | D |
| WX605 | D | D |
| WX606 | C | D |
| WX591 | B | C |
| WX612 | D | D |
| WX613 | B | C |
| WX614 | A | B |
| WX615 | D | D |
| WX611 | B | C |
| WX550 | C | D |
| WX551 | C | D |
| WX552 | B | C |
| WX579 | C | D |
| WX580 | C | D |
| WX581 | C | D |
| WX593 | D | D |
| WX592 | D | D |
| WX604 | C | D |
| WX605 | D | D |
| WX606 | C | D |
| WX591 | B | C |
| WX612 | D | D |
| WX613 | B | C |
| WX614 | A | B |
| WX615 | D | D |
| WX611 | B | C |

A ≤ 10 nM;
10 < B ≤ 100 nM;
100 < C ≤ 1000 nM;
D1 > 1000 nM

Pharmacokinetic (PK) Test

The clear solution obtained by dissolving the test compound was respectively administrated by tail vein injection and gavage into the mice DBA/1 mice (overnight fasting, 7 to 8 weeks old). After administration of the test compound, the mice in the vein injection group at 0.083, 0.25, 0.5, 1, 2, 4, 8 and 24 hours, and gavage group at 0.25, 0.5, 1, 2, 4, 8 and 24 hours, blood is collected from the mandibular vein and centrifuged to obtain plasma. The plasma concentration was determined by LC-MS/MS. The pharmacokinetic parameters were calculated by non-compartmental model linear logarithmic trapezoid method with using WinNonlin™ Version 6.3 pharmacokinetic software.

TABLE 2-1

The PK test results of WX552 in mice

| PK Parameters | Mean |
|---|---|
| $T_{1/2}$ (hr) | 1.18 |
| $C_{max}$ (nM) | 3723 |
| $AUC_{0\text{-}inf}$ (nM · hr) | 11448 |
| Bioavailability (%)$^a$ | 74.39 |

TABLE 2-2

The PK test results of WX591 in mice

| PK Parameters | Mean |
|---|---|
| $T_{1/2}$ (hr) | 2.26 |
| $C_{max}$ (nM) | 3017 |
| $AUC_{0\text{-}inf}$ (nM · hr) | 10467 |
| Bioavailability (%)$^a$ | 87.0 |

TABLE 2-3

The PK test results of WX614 in mice

| PK Parameters | Mean |
|---|---|
| $T_{1/2}$ (h) | 1.76 |
| $C_{max}$ (nM) | 3087 |
| $AUC_{0\text{-}inf}$ (nM · h) | 10200 |
| Bioavailability (%)$^a$ | 73.9 |

The compounds WX552, WX591 and WX614 of the present invention have good oral bioavailability and higher exposure in mice, which is beneficial to produce in vivo pharmacological effects.

Rat Adjuvant-Induced Arthritis Model Efficacy Test

The effect of the compounds of the present invention on the treatment of arthritis was verified by rat adjuvant arthritis models.

Female, Lewis rats with body weight 160-180 g were anesthetized with isoflurane and was injected with 0.1 ml of *mycobacterium tuberculosis* suspension subcutaneously in the left posterior foot. After modeling for 13 days, the corresponding test compound was administrated, such as that the rats were respectively administrated with 1 mpk, 3 mpk, 10 mpk of the test compound WX614, 10 mpk of the test compound WX552, and 10 mpk of the test compound WX591 dissolved in a mixed solvent of DMSO/PEG400/H₂O, and orally administrated to female Lewis rats (10 rats in each dose group). Two weeks after continuous administration, the state of the rats was observed and the volume of the swollen foot was recorded and scored. The experiments showed that all the compounds of the present invention WX614, WX552 and WX591 exhibit good arthritis inhibitory activity.

TABLE 3-1

| Compound | Dose (mg/kg) | AUC (%) |
|---|---|---|
| Solvent Control Group | 0 | 0% |
| Compound WX552 | 10 | 31.7 |

TABLE 3-1-continued

| Compound | Dose (mg/kg) | AUC (%) |
|---|---|---|
| Compound WX591 | 10 | 44.7 |
| Compound WX614 | 1 | 20.2 |
|  | 3 | 50.2 |
|  | 10 | 61.8 |

Mouse Collagen-Induced Arthritis Model Efficacy Test

The effect of the compounds of the present invention on the treatment of arthritis was verified by the mouse collagen-induced arthritis model.

The DBA/1 male mice were selected and injected subcutaneously with the emulsions of collagen and Freund's complete adjuvant at base of tail on day 0 and day 21, and on day 29 the mice was divided into groups. The compound WX6144 (3 mpk, 10 mpk, 30 mpk) was dissolved in DMSO/PEG400/H₂O [5/20/75 (v/v/v)] and administered orally to CIA mice (Shanghai SLAC Laboratory Animal Co., Ltd, 10 mice in each dose group), and the mice were continuously administrated for 2 weeks, the weight of mice were recorded and the arthritis of mice was clinically scored. The results showed that the compound WX614 of the present invention had a significant therapeutic effect on mouse rheumatoid arthritis.

TABLE 3-2

| Compound | Dose (mg/kg) | AUC (%) |
|---|---|---|
| Solvent Control Group | 0 | 0 |
| Compound WX614 | 3 | 42.4 |
|  | 10 | 51.3 |
|  | 30 | 82.5 |

The invention claimed is:
1. A compound of Formula (I):

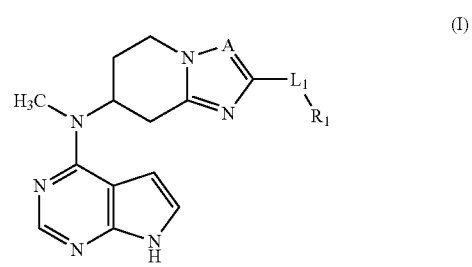

or a pharmaceutically acceptable salt thereof,
wherein:
A is selected from C(R) or N;
L₁ is selected from a single bond, —C(=O)O—, —C(=O)—, —S(=O)—, —S(=O)₂—, —C(=O)N(R)—, —N(R)C(=O)N(R)—, —N(R)—, —S(=O)N(R)—, —S(=O)₂N(R)C(R)₂— or —S(=O)N(R)C(R)₂—;
R₁ is selected from H, CN, OH, NH₂, halogen, $C_{1\text{-}6}$ alkyl, $C_{1\text{-}6}$ heteroalkyl, $C_{3\text{-}6}$ cycloalkyl or 3-6 membered heterocycloalkyl, wherein the $C_{1\text{-}6}$ alkyl, $C_{1\text{-}6}$ heteroalkyl, $C_{3\text{-}6}$ cycloalkyl or 3-6 membered heterocycloalkyl is optionally substituted with 1, 2, 3 or 4 R;
R is independently selected from H, CN, OH, NH₂, halogen, $C_{1\text{-}6}$ alkyl or $C_{1\text{-}6}$ heteroalkyl, wherein the C<sub>1-6</sub> alkyl and C<sub>1-6</sub> heteroalkyl are independently and optionally substituted with 1, 2, 3 or 4 R'; and R' is selected from halogen, OH, $NH_2$, CN, $CH_3$, $CH_2CH_3$, $CF_3$, $CH_2CF_3$, $NHCH_3$ or $N(CH_3)_2$;

wherein hetero is a heteroatom or a heterogroup selected from the group consisting of N, O, S, —C(=O)O—, —C(=O)—, —S(=O)— and —S(=O)$_2$—, and the number of heteroatoms or heterogroups in any of the above conditions is independently selected from 1, 2 or 3.

2. The compound according to claim 1, or a pharmaceutically acceptable salt thereof, wherein:

$L_1$ is selected from a single bond, —C(=O)O—, —C(=O)—, —S(=O)—, —S(=O)$_2$—, —C(=O)NH—, —NHC(=O)NH—, —NH—, —S(=O)NH—, —S(=O)$_2$NHCH$_2$— or —S(=O)NHCH$_2$—.

3. The compound according to claim 1, or a pharmaceutically acceptable salt thereof, wherein:

$R_1$ is selected from H, CN, OH, $NH_2$, $C_{1-3}$ alkyl, $C_{1-2}$ alkyl-N(CH$_3$)$_2$, $C_{1-2}$ alkyl-N(CH$_2$CH$_3$)$_2$, $C_{1-2}$ alkyl-NHCH$_3$, $C_{1-2}$ alkyl-NHCH$_2$CH$_3$, $C_{1-3}$ alkyl-S(=O)$_2$—$C_{1-3}$ alkyl, $C_{1-3}$ alkyl-S(=O)—$C_{1-3}$ alkyl, $C_{4-5}$ cycloalkyl or 4-5 membered heterocycloalkyl, wherein the $C_{1-3}$ alkyl, $C_{1-2}$ alkyl-N(CH$_3$)$_2$, $C_{1-2}$ alkyl-N(CH$_2$CH$_3$)$_2$, $C_{1-2}$ alkyl-NHCH$_3$, $C_{1-2}$ alkyl-NHCH$_2$CH$_3$, $C_{1-3}$ alkyl-S(=O)$_2$—$C_{13}$ alkyl, $C_{1-3}$ alkyl-S(=O)—$C_{13}$ alkyl, $C_{4-5}$ cycloalkyl or 4-5 membered heterocycloalkyl is optionally substituted with 1, 2, 3 or 4 R.

4. The compound according to claim 3, or a pharmaceutically acceptable salt thereof, wherein:

$R_1$ is selected from CN, $CH_3$, $CH_2CH_3$, $(CH_2)_2CH_3$, $CH_2NHCH_3$, $(CH_2)_2$—S(=O)$_2$—$CH_3$ or cyclobutyl, wherein the $CH_3$, $CH_2CH_3$, $(CH_2)_2CH_3$, $CH_2NHCH_3$, $(CH_2)_2$—S(=O)$_2$—$CH_3$ or cyclobutyl is optionally substituted with 1, 2, 3 or 4 R.

5. The compound according to claim 4, or a pharmaceutically acceptable salt thereof, wherein:

$R_1$ is selected from CN, $CH_3$, $CH_2CHF_2$, $CH_2CF_3$, $(CH_2)_2CN$, $(CH_2)_2CHF_2$, $CH_2NHCH_3$, $(CH_2)_2$—S(=O)$_2$—$CH_3$ or 3,3-difluorocyclobutyl.

6. The compound according to claim 1, or a pharmaceutically acceptable salt thereof, wherein:

R is independently selected from H, CN, OH, $NH_2$, halogen, $CH_3$, $CH_2CH_3$, $(CH_2)_2CH_3$, $CH(CH_3)_2$, $NHCH_3$, $N(CH_3)_2$ or $NH(CH_3)_2^+$, wherein the $CH_3$, $CH_2CH_3$, $(CH_2)_2CH_3$, $CH(CH_3)_2$, $NHCH_3$, $N(CH_3)_2$ and $NH(CH_3)_2^+$ are independently and optionally substituted with 1, 2 or 3 R'.

7. The compound according to claim 6, or a pharmaceutically acceptable salt thereof, wherein:

$L_1$ is selected from a single bond, —C(=O)O—, —C(=O)—, —S(=O)—, —S(=O)$_2$—, —C(=O)NH—, —NHC(=O)NH—, —NH—, —S(=O)NH—, —S(=O)$_2$NHCH$_2$— or —S(=O)NHCH$_2$—.

8. The compound according to claim 6, or a pharmaceutically acceptable salt thereof, wherein:

$R_1$ is selected from H, CN, OH, $NH_2$, $C_{1-3}$ alkyl, $C_{1-2}$ alkyl-N(CH$_3$)$_2$, $C_{1-2}$ alkyl-N(CH$_2$CH$_3$)$_2$, $C_{1-2}$ alkyl-NHCH$_3$, $C_{1-2}$ alkyl-NHCH$_2$CH$_3$, $C_{1-3}$ alkyl-S(=O)$_2$—$C_{1-3}$ alkyl, $C_{1-3}$ alkyl-S(=O)—$C_{1-3}$ alkyl, $C_{4-5}$ cycloalkyl or 4-5 membered heterocycloalkyl, wherein the $C_{1-3}$ alkyl, $C_{1-2}$ alkyl-N(CH$_3$)$_2$, $C_{1-2}$ alkyl-N(CH$_2$CH$_3$)$_2$, $C_{1-2}$ alkyl-NHCH$_3$, $C_{1-2}$ alkyl-NHCH$_2$CH$_3$, $C_{1-3}$ alkyl-S(=O)$_2$—$C_{13}$ alkyl, $C_{1-3}$ alkyl-S(=O)—$C_{13}$ alkyl, $C_{4-5}$ cycloalkyl or 4-5 membered heterocycloalkyl is optionally substituted with 1, 2, 3 or 4 R.

9. The compound according to claim 8, or a pharmaceutically acceptable salt thereof, wherein:

$R_1$ is selected from CN, $CH_3$, $CH_2CH_3$, $(CH_2)_2CH_3$, $CH_2NHCH_3$, $(CH_2)_2$—S(=O)$_2$—$CH_3$ or cyclobutyl, wherein the $CH_3$, $CH_2CH_3$, $(CH_2)_2CH_3$, $CH_2NHCH_3$, $(CH_2)_2$—S(=O)$_2$—$CH_3$ or cyclobutyl is optionally substituted with 1, 2, 3 or 4 R.

10. The compound according to claim 9, or a pharmaceutically acceptable salt thereof, wherein:

$R_1$ is selected from CN, $CH_3$, $CH_2CHF_2$, $CH_2CF_3$, $(CH_2)_2CN$, $(CH_2)_2CHF_2$, $CH_2NHCH_3$, $(CH_2)_2$—S(=O)$_2$—$CH_3$ or 3,3-difluorocyclobutyl.

11. The compound according to claim 1, wherein the compound is selected from the group consisting of:

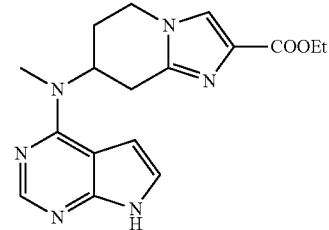

WX550

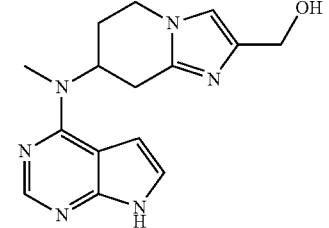

WX551

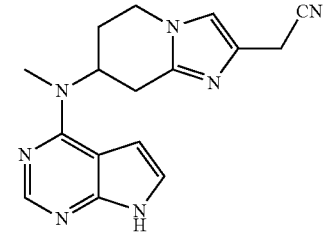

WX552

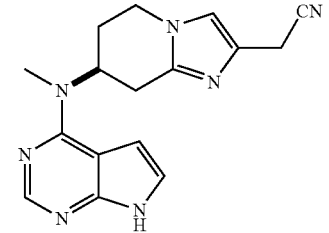

WX612

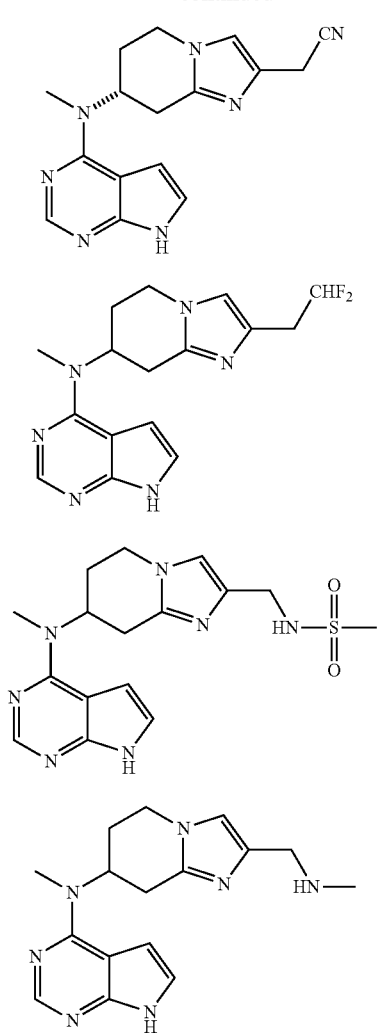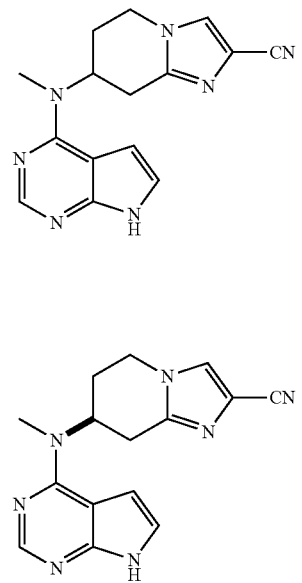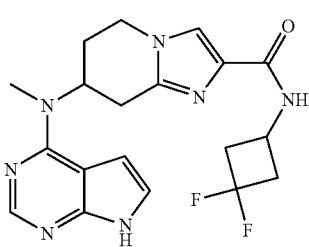

12. A pharmaceutical composition comprising a therapeutically effective amount of a compound according to claim 1, or a pharmaceutically acceptable salt thereof, and a pharmaceutically acceptable carrier.

13. A pharmaceutical composition comprising a therapeutically effective amount of a compound according to claim 6, or a pharmaceutically acceptable salt thereof, and a pharmaceutically acceptable carrier.

14. A method for inhibiting Janus kinase activity in a subject, comprising administering to a subject in need thereof a therapeutically effective amount of a compound according to claim 1.

15. The method according to claim 14, wherein the subject has arthritis.

16. The method according to claim 15, wherein the arthritis is rheumatoid arthritis.

17. A method for inhibiting Janus kinase activity in a subject, comprising administering to a subject in need thereof a therapeutically effective amount of the pharmaceutical composition according to claim 12.

18. The method according to claim 17, wherein the subject has arthritis.

19. The method according to claim 18, wherein the arthritis is rheumatoid arthritis.

20. A process for the preparation of a compound of Formula (I):

wherein:
A is CH;
$L_1$ is —C(=O)NH—;
$R_1$ is selected from H, CN, OH, $NH_2$, halogen, $C_{1-6}$ alkyl, $C_{1-6}$ heteroalkyl, $C_{3-6}$ cycloalkyl or 3-6 membered heterocycloalkyl, wherein the $C_{1-6}$ alkyl, $C_{1-6}$ heteroalkyl, $C_{3-6}$ cycloalkyl or 3-6 membered heterocycloalkyl is optionally substituted with 1, 2, 3 or 4 R;
R is independently selected from H, CN, OH, $NH_2$, halogen, $C_{1-6}$ alkyl or $C_{1-6}$ heteroalkyl, wherein the $C_{1-6}$ alkyl and $C_{1-6}$ heteroalkyl are independently and optionally substituted with 1, 2, 3 or 4 R'; and
R' is selected from halogen, OH, $NH_2$, CN, $CH_3$, $CH_2CH_3$, $CF_3$, $CH_2CF_3$, $NHCH_3$ or $N(CH_3)_2$;

wherein hetero is a heteroatom or a heterogroup selected from the group consisting of N, O, S, —C(=O)O—, —C(=O)—, —S(=O)— and —S(=O)$_2$—, and the number of heteroatoms or heterogroups in any of the above conditions is independently selected from 1, 2 or 3;
comprising the following steps:
(1) reacting a compound of the formula:

wherein:
A is CH;
$L_1$ is —C(=O)O—;
$R_1$ is H; and
PG is selected from benzyloxycarbonyl, tert-butoxycarbonyl, fluorenylmethoxycarbonyl, allyloxycarbonyl, trimethylethoxycarbonyl, methoxycarbonyl, ethoxycarbonyl, o-phthalyl, p-toluenesulfonyl, trifluoroacetyl, benzyl or p-methoxybenzyl;
with sodium hydroxide in the presence of tetrahydrofuran and a protic cosolvent, to provide a compound of the formula:

wherein:
A is CH;
$L_1$ is —C(=O)O—; and
$R_1$ is H; and
(2) reacting the compound of the formula:

wherein:
A is CH;
$L_1$ is —C(=O)O—; and
$R_1$ is H;

with a compound of the formula:

wherein:
- $R_1$ is selected from H, CN, OH, $NH_2$, halogen, $C_{1-6}$ alkyl, $C_{1-6}$ heteroalkyl, $C_{3-6}$ cycloalkyl or 3-6 membered heterocycloalkyl, wherein the $C_{1-6}$ alkyl, $C_{1-6}$ heteroalkyl, $C_{3-6}$ cycloalkyl or 3-6 membered heterocycloalkyl is optionally substituted with 1, 2, 3 or 4 R;
- R is independently selected from H, CN, OH, $NH_2$, halogen, $C_{1-6}$ alkyl or $C_{1-6}$ heteroalkyl, wherein the $C_{1-6}$ alkyl and $C_{1-6}$ heteroalkyl are independently and optionally substituted with 1, 2, 3 or 4 R'; and
- R' is selected from halogen, OH, $NH_2$, CN, $CH_3$, $CH_2CH_3$, $CF_3$, $CH_2CF_3$, $NHCH_3$ or $N(CH_3)_2$;
- wherein hetero is a heteroatom or a heterogroup selected from the group consisting of N, O, S, —C(=O)O—, —C(=O)—, —S(=O)— and —S(=O)$_2$—, and the number of heteroatoms or heterogroups in any of the above conditions is independently selected from 1, 2 or 3;
- in the presence of pyridine, to provide the compound of Formula (I) above.

\* \* \* \* \*